(12) United States Patent
Musselman

(10) Patent No.: US 8,558,170 B1
(45) Date of Patent: Oct. 15, 2013

(54) SAMPLING SYSTEM FOR USE WITH SURFACE IONIZATION SPECTROSCOPY

(71) Applicant: IonSense, Inc., Saugus, MA (US)

(72) Inventor: Brian D. Musselman, Melrose, MA (US)

(73) Assignee: Ionsense, Inc., Saugus, MA (US)

( * ) Notice: Subject to any disclaimer, the term of this patent is extended or adjusted under 35 U.S.C. 154(b) by 0 days.

(21) Appl. No.: 13/797,114

(22) Filed: Mar. 12, 2013

Related U.S. Application Data

(60) Continuation of application No. 13/541,727, filed on Jul. 4, 2012, which is a division of application No. 12/683,257, filed on Jan. 6, 2010, now Pat. No. 8,217,341, which is a division of application No. 11/580,323, filed on Oct. 13, 2006, now Pat. No. 7,700,913.

(60) Provisional application No. 60/778,874, filed on Mar. 3, 2006.

(51) Int. Cl.
*H01J 49/04* (2006.01)

(52) U.S. Cl.
CPC .................................. *H01J 49/04* (2013.01)
USPC ....................................................... 250/288

(58) Field of Classification Search
USPC .................................................. 250/288, 281
See application file for complete search history.

(56) References Cited

U.S. PATENT DOCUMENTS

| | | | | |
|---|---|---|---|---|
| 4,641,541 A | * | 2/1987 | Sharp | 73/864.81 |
| 4,662,914 A | * | 5/1987 | Hansen et al. | 96/106 |

* cited by examiner

*Primary Examiner* — Kiet T Nguyen
(74) *Attorney, Agent, or Firm* — Sci-Law Strategies, PC

(57) ABSTRACT

In various embodiments of the invention, a device permits more efficient collection and transmission of ions produced by the action of a carrier gas containing metastable neutral excited-state species into a mass spectrometer. In one embodiment of the invention, the device incorporates the source for ionization in combination with a jet separator to efficiently remove excess carrier gas while permitting ions to be more efficiently transferred into the vacuum chamber of the mass spectrometer. In an embodiment of the invention, improved collection of ions produced by the carrier gas containing metastable neutral excited-state species at greater distances from between the position of the analyte and the position of the mass spectrometer are enabled.

20 Claims, 22 Drawing Sheets

SAMPLING SYSTEM FOR USE WITH SURFACE IONIZATION SPECTROSCOPY

PRIORITY CLAIM

This application is a continuation of U.S. Utility patent application Ser. No. 13/541,727 entitled: "Sampling System For Use With Surface Ionization Spectroscopy", inventor: Brian D. Musselman filed Jul. 4, 2012 which claims priority to U.S. Utility patent application Ser. No. 12/683,257, which issued Jul. 10, 2012 as U.S. Utility Pat. No. 8,217,341 entitled: "Sampling System For Use With Surface Ionization Spectroscopy", inventor: Brian D. Musselman, filed Jan. 6, 2010 and is a divisional of U.S. Utility patent application Ser. No. 11/580,323, which issued Apr. 20, 2010 as U.S. Utility Pat. No. 7,700,913 entitled: "Sampling System For Use With Surface Ionization Spectroscopy", inventor: Brian D. Musselman, filed Oct. 13, 2006, which claims priority to U.S. Provisional Patent Application Ser. No. 60/778,874, entitled: "Sampling System For Use With Surface Ionization Spectroscopy", inventor: Brian D. Musselman, filed Mar. 3, 2006. These applications are herein expressly incorporated by reference in their entireties.

CROSS REFERENCE TO RELATED APPLICATION

This application is related to the following application: "Sampling System For Use With Surface Ionization Spectroscopy", inventor: Brian D. Musselman, application Ser. No. 12/275,079, filed on Nov. 20, 2008.

FIELD OF THE INVENTION

The present invention relates to the improved collection and transfer of analyte ions and neutral molecules for more efficient sampling by a spectroscopy system.

BACKGROUND OF THE INVENTION

Since the invention of the gas effusion separator in the 1960's by Watson and Biemann and its improvement, the jet separator, invented by Ryhage, it has been possible to efficiently remove carrier gases from the flow of gaseous molecules exiting the end of a Gas Chromatography (GC) column. The gases commonly used in the GC experiment include Helium, Hydrogen, and Nitrogen. In all cases described in the literature the species passing through the jet separator are present as neutral atoms and molecules. The molecules exiting from the jet separator directly enter into the mass spectrometer (MS) where they are ionized in an ionization source, which is operating under high vacuum conditions. The prime function of the jet separator used in GC/MS is to remove the carrier gas while enriching the flow of neutral molecules of analyte molecules into the mass spectrometer.

In contrast to the GC instrument, an atmospheric pressure ionization (API) instrument generates ions external to a mass spectrometer high vacuum system. This being the case, the majority of API source MS instruments generate ions in the presence of an electrical field. This electric field is also used to direct the ions formed during the ionization process towards the inlet of the MS. In desorption electrospray ionization (DESI) and other desorption ionization techniques, the generation of ions at atmospheric pressure can be accomplished with the sample at ground potential. For example, there is often no component of the system to which an electrical potential can be applied in order to selectively focus ions towards the mass spectrometer inlet. In these circumstances, the transfer of ions into the inlet of the MS relies in large part on the action of the vacuum to draw the ions into the MS inlet. MS sources often contain multiple pumping stages separated by small orifices, which serve to reduce the gas pressure along the path that the ions of interest travel to an acceptable level for mass analysis; these orifices also operate as ion focusing lenses when electrical potential is applied to their surface.

A desorption ionization source allowing desorption and ionization of molecules from surfaces, ionization direct from liquids and ionization of molecules in vapor was recently developed by Cody et al. This method utilizes low mass atoms or molecules including Helium, Nitrogen and other gases that can be present as long lived metastables as a carrier gas. These carrier gas species are present in high abundance in the atmosphere where the ionization occurs.

While this ionization method offers a number of advantages for rapid analysis of analyte samples, there remain encumbrances to the employment of this technique for a variety of samples and various experimental circumstances. For example, it would be advantageous to increase the sensitivity of the desorption ionization technique by improving the transfer efficiency of sample related ions from their point of generation to the mass analyzer of the mass spectrometer. Further, it would be desirable to be able to direct the desorption ionization source at an analyte sample at a significant distance from the mass spectrometer. In addition, desorption ionization would have more impact if it was possible to utilize the technique on conventional high vacuum ionization sources encountered in most mass spectrometers.

SUMMARY OF THE INVENTION

Embodiments of this invention include devices and methods for collecting and transferring analyte ions formed within a carrier gas to the inlet of a mass spectrometer. In embodiments of the invention, the carrier gas contains metastable neutral excited-state species, charged and neutral molecules. In other embodiments of the invention, a jet separator is used to more efficiently transfer ions and molecules into a high vacuum region of the mass spectrometer. In contrast to the prior art, which only describes the use of jet separators for enriching the transfer of molecules into the MS; in embodiments of the invention a jet separator is used to selectively enrich the transfer of ions by separating those ions from the carrier gas. Using the jet separator, the sensitivity of desorption ionization techniques can be increased by allowing the sampling of a significantly greater carrier gas volume per unit of time where the abundance of ions per unit volume of the carrier gas is uniform at its inlet. Further, using the jet separator as the first vacuum stage of pumping with the desorption ionization source permits more efficient collection of analyte at a significant distance from the mass spectrometer. In addition, with a jet separator desorption ionization source can be coupled with a conventional high vacuum ionization source mass spectrometer.

While external ion sources are known for use with MS, the problem of transporting sufficient ions to the MS typically results in lowered sensitivity. The problem is exacerbated with an external ionization source operated at or near atmospheric pressure, since the MS typically operates at high vacuum. Jet separators were previously used to isolate an analyte of interest from a carrier gas prior to entry of the neutral analyte molecules into a MS. However, the principle of using a jet separator together with an external ion source to introduce ions into the MS has not previously been appreciated. Thus in one embodiment of the invention, a gas separator consists of an external ion source and a jet separator. In an embodiment, such a gas separator is used in a MS. In various embodiments of the invention, a gas separator can be any device capable of stripping small neutral atoms or molecules away from a charged species being transferred into a high vacuum region. In alternative embodiments of the invention, electric fields can be applied to surfaces of the gas separator to improve the transmission of ions into the MS.

In various embodiments of the invention, the gas separator comprises a source of ions, a plurality of tubes with a gap between the tubes and a vacuum. Typically the gas separator is made up of an inlet tube and an outlet tube where the proximal end of the inlet tube is closest to the external ionization source and the distal end is furthest from the external ionization source. The vacuum can be applied at the exit of at least one of the distal tubes and can also be applied at one or more of the gap between the plurality of tubes. In various embodiments wire mesh screens can enclose the gap between the plurality of tubes.

The proximal end of the inlet tube is typically a Z-axis distance from the external ionization source of between a lower limit of approximately $10^{-3}$ m and an upper limit of approximately $10^1$ m. A heater for heating, the proximal and/or the distal end of the inlet tube and the proximal and/or the distal end of the outlet tube, can be used with the gas separator. In alternative embodiments of the invention, one or more capacitive surface on the one or more inlet and/or outlet tubes to which one or more potential can be applied.

BRIEF DESCRIPTION OF THE DRAWINGS

Various embodiments of the present invention will be described in detail based on the following figures, wherein.

DETAILED DESCRIPTION OF THE INVENTION

Figure 1:
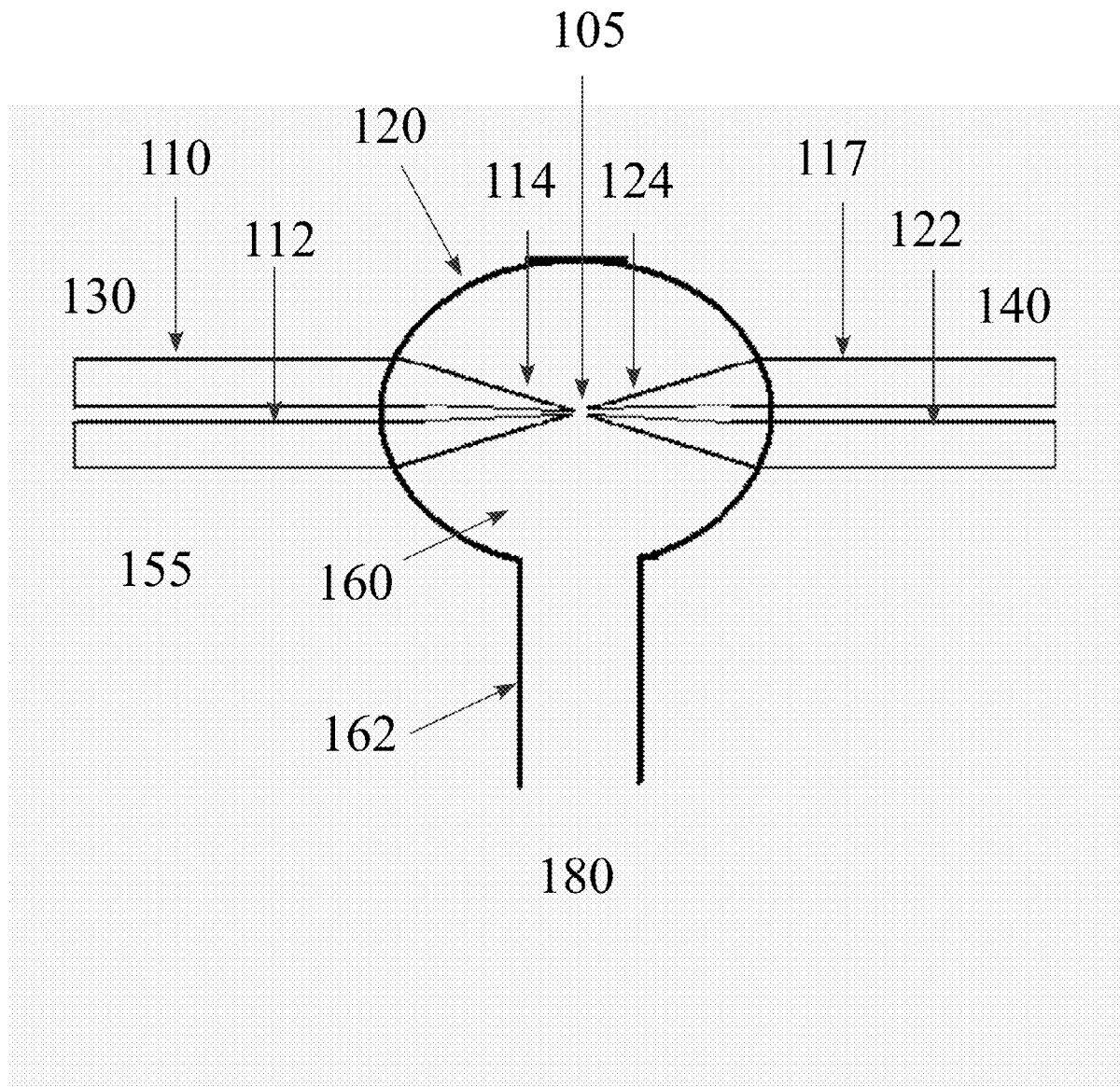
FIG. 1 is a diagram of a prior art jet separator as used with a conventional GC/MS instrument.

The term jet separator will be used to refer to the prior art. The term gas separator will not be used to refer to the prior art. The term jet separator may also be used to refer to a charged species and/or a neutral molecule separator. The term gas separator will be used to refer to a charged species and/or a neutral molecule separator. The term 'inlet tube' will be used to refer to the low vacuum side of the gas separator. The term 'exit tube' may be used to refer to the high vacuum side of the gas separator. The term 'outlet tube' will be used to refer to the high vacuum side of the gas separator.

The recent development of a non-radioactive Atmospheric Pressure Ionization (API) method for ionization of analytes as described in U.S. Pat. No. 6,949,741 which is hereinafter referred to as the '741 patent and which is herein expressly incorporated by reference in its entirety allows for the Direct Analysis in Real Time (DART®) of analyte samples. The '741 patent discloses a means for desorption ionization of molecules from surfaces, liquids and vapor using a carrier gas containing metastable neutral excited-state species. The device described in the '741 patent utilizes a large volume of carrier gas that is typically Helium and/or Nitrogen although other inert gases that can generate metastable neutral excited-state species may be used.

Since the invention of the gas effusion separator in the 1960's by Watson and Biemann and its improvement, the jet separator, invented by Ryhage (U.S. Pat. No. 3,633,027 which is herein expressly incorporated by reference in its entirety), it has been possible to efficiently remove carrier gases from the flow of gaseous molecules exiting the end of a Gas Chromatography (GC) column. The jet separator device enabled the commercial development of gas chromatography/mass spectrometry (GC/MS) systems. In the GC/MS, gas flow through the wide bore GC column ranged from 20 to 30 milliliters per minute. These instruments were extensively used starting in the 1970's and until the late 1980's when low flow capillary GC column instruments were adopted as the industry standard, thus removing the need for the jet separator. The gases commonly used in the GC experiment include Helium, Hydrogen, and Nitrogen. The molecules exiting from the jet separator directly enter into the mass spectrometer where they are ionized by an ionization source, which is operating under high vacuum conditions. A vacuum of atmospheric pressure is 1 torr. Generally, 'approximately' in this pressure range encompasses a range of pressures from below $10^1$ ton to $10^{-1}$ torr. A vacuum of below $10^{-3}$ torr would constitute a high vacuum. Generally, 'approximately' in this pressure range encompasses a range of pressures from below $5\times10^{-3}$ torr to $5\times10^{-6}$ torr. A vacuum of below $10^{-6}$ torr would constitute a very high vacuum. Generally, 'approximately' in this pressure range encompasses a range of pressures from below $5\times10^{-6}$ torr to $5\times10^{-9}$ torr. In the following, the phrase 'high vacuum' encompasses high vacuum and very high vacuum. The prime function of the jet separator is to remove the carrier gas while increasing the efficiency of transfer of neutral molecules including analyte molecules into the mass spectrometer. After the improvements introduced by Ryhage in the jet separator, Dawes et al. describe a molecular separator in detail in U.S. Pat. No. 5,137,553 and a variable molecular separator in U.S. Pat. No. 4,654,052, which are both herein expressly incorporated by reference in their entirety.

In contrast to the GC/MS instrument, the API-MS provides the means to generate ions external to a mass spectrometer high vacuum system. This being the case, the majority of API source instruments generate ions in the presence of an electrical field. This electric field is also used to direct the ions formed during the ionization process towards the inlet of the Mass Spectrometer (MS). The electric field is typically established by placing a potential on a needle or tube through which a solution containing dissolved analyte molecules flows. In these API-MS instruments the high vacuum inlet is integrated into the instrument design facilitating reduction of gas flow and focusing of ions into the high vacuum chamber of the mass spectrometer. The action of focusing ions into the mass spectrometer is completed when the potential applied to the inlet and that applied to the needle where the ionization act together to transfer ions selectively into the mass spectrometer, while the majority of neutral molecules and atmospheric gases diffuse away into the surrounding atmosphere.

The DART® ionization source developed by Cody et al. and described in the '741 patent, is a method for desorption of ions at atmospheric pressure. DART® utilizes low mass atoms or molecules including Helium, Nitrogen and other gases that can be present as long lived metastables as a carrier gas. These carrier gas species are present in high abundance in the atmosphere where DART® ionization occurs.

In DART® and DESI, the generation of ions at atmospheric pressure can be accomplished with the sample at ground potential. In the case of desorption with these ionization sources there are situations in which there is no component of the system to which an electrical potential can be applied in order to selectively focus ions towards the mass spectrometer inlet. The process relies in large part on the action of the vacuum to draw the ions into the inlet of the MS. Prior art in API-MS includes many systems where single lenses as well as a plurality of lenses act as ion focusing elements, positioned in the ion formation region, to effect ion focusing post-ionization at atmospheric pressure. Ions formed in the atmospheric pressure region are selectively drawn to or forced towards the mass spectrometer inlet by the action of the electrical potential applied to these focusing elements. Atmospheric pressure sources often contain multiple pumping stages separated by small orifices. The multiple pumping stages serve to reduce the gas pressure to an acceptable level for mass analysis, along the path that the ions of interest travel. The orifices also operate as ion focusing lenses when electrical potential is applied to their surface. Alternate API-MS designs use a length of narrow diameter capillary tube to reduce the gas pressure in place of the multiple element stages. In these designs the area surrounding the capillary inlet is either a metal coated glass surface or metal piece to which an electrical potential may be applied.

FIG. 1 shows the prior art jet separator 120, made up of an inlet side 130 and an outlet side 140. The stream of analyte molecules dispersed in a stream of carrier gas molecules travel through the inside diameter 112, exit the inlet side of the jet separator 110 at an orifice 114. The analyte molecules traverse the gap 105 and are sucked through the orifice 124 into the inner diameter 122 of the outlet side of the jet separator 117. The lighter mass carrier gas molecules once exiting the inlet tip 114 are drawn by the lower relative pressure in the region 160 compared with the region 155 outside the chamber 162 formed by the vacuum 180.

Figure 2:
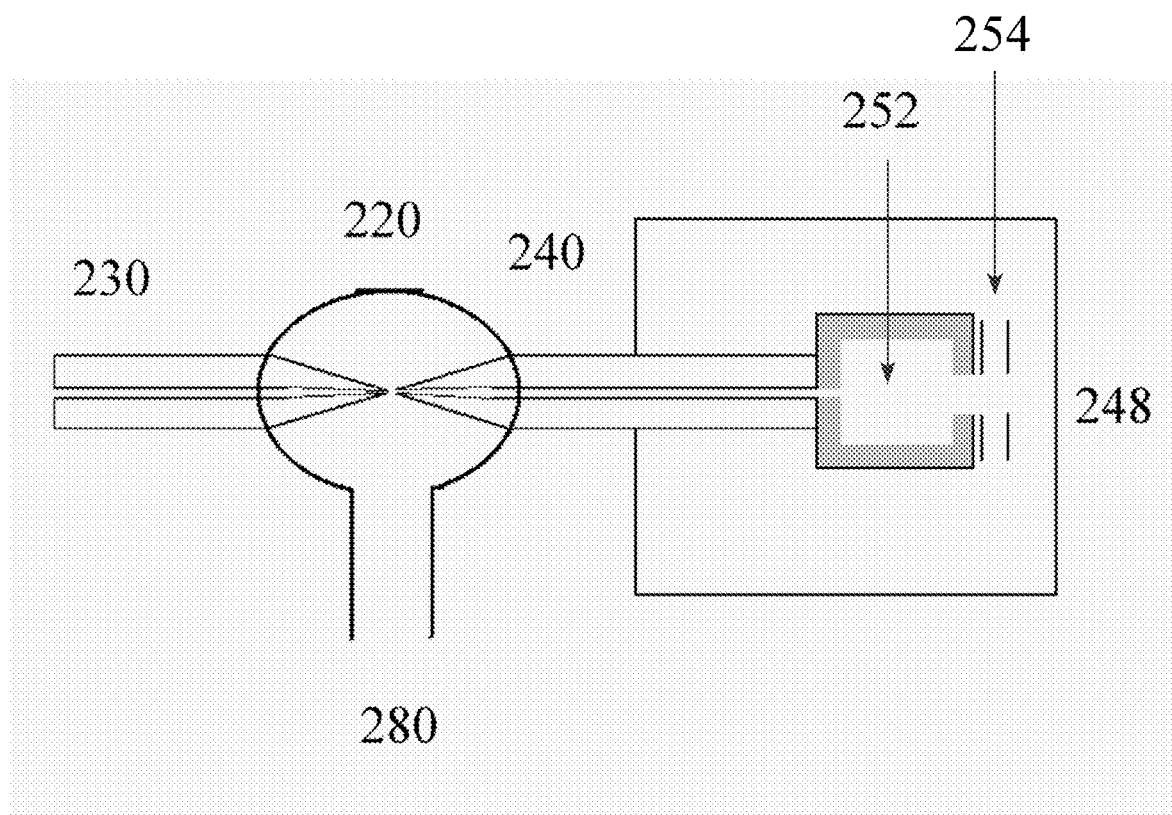
FIG. 2 is a schematic diagram of a prior art jet separator with a conventional GC/MS high vacuum ionization source.

FIG. 2 shows the prior art transfer of ions directly to a source region 240 of a mass spectrometer where a region around a conventional ionization source 252 is under high vacuum. Typically, neutral molecules and gases exit 230 a chromatographic column entering a conventional jet separator 220 where the gas is selectively removed under a vacuum 280 while the heavier mass molecules pass into a source 252 where they are ionized and subsequently are pushed by the action of the electrical field in the source 252 thru a series of lenses 254 for focusing before entering the mass analyzer 248 for analysis.

Figure 3:
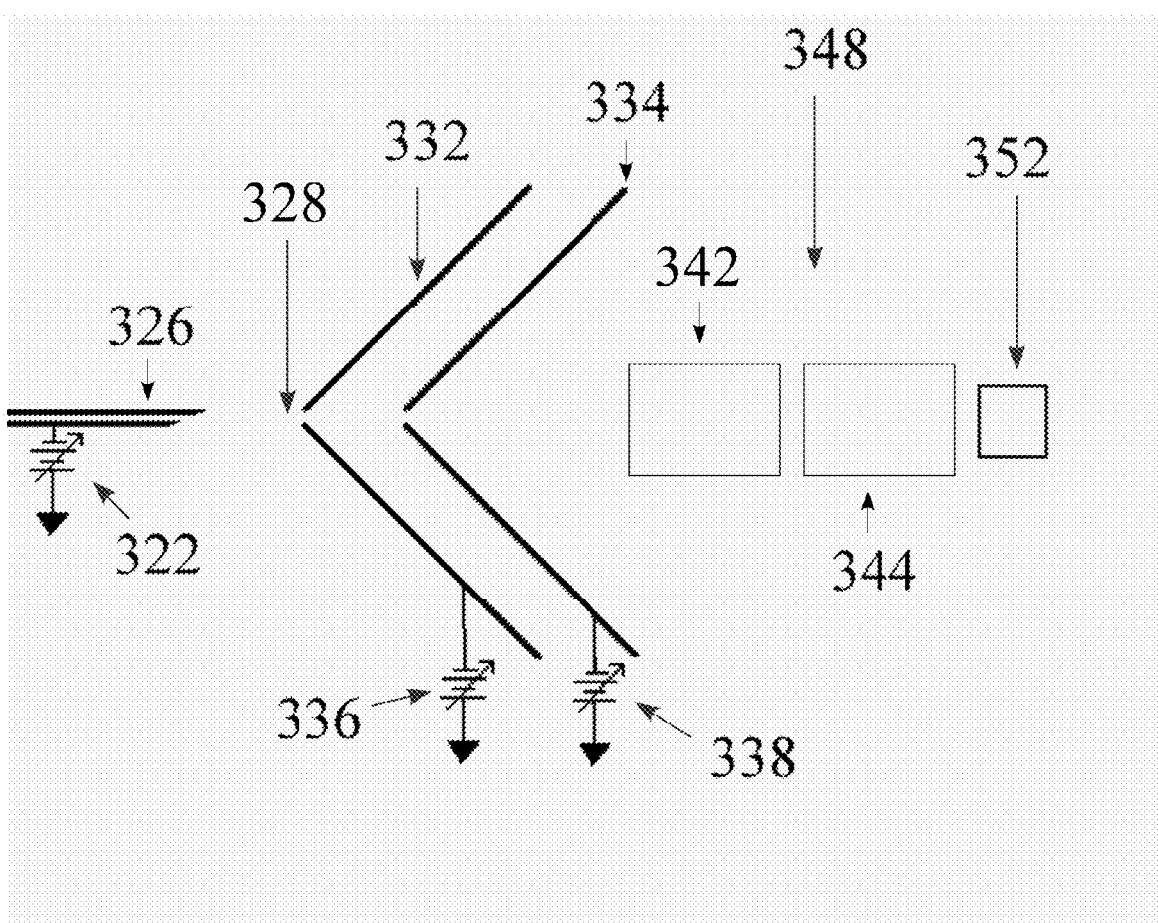
FIG. 3 is a schematic diagram of a typical API-MS of the prior art.

FIG. 3 shows the prior art device used for transfer of ions directly to a mass spectrometer vacuum inlet of an atmospheric pressure ionization mass spectrometer (API-MS) instrument. The ionization source for an API-MS typically includes a needle or tube 326 to which a potential 322 is applied. The needle 326 is aligned with an orifice 328 of a series of one or more skimmers 332, 334 that operate as an ion-focusing lens when electrical potentials 336 338 are applied to the skimmer 332, 334 surfaces in order to direct the ions into one or more mass analyzers 342, 344 aligned to permit transfer of ions to an ion detector 352. The orifice also provides a boundary between pumping stages, which serves to reduce the gas pressure, along a path that ions of interest travel, to an acceptable level for a mass analyzer 348 and ion detector 352 to function properly.

A conventional jet separator in the GC/MS experiment separates analyte molecules from a carrier gas using a vacuum. In the DART® experiment, the analyte ions are present with a carrier gas. The gases that jet separators have been typically designed to selectively remove carrier gas from analyte molecules are the same or similar to the typical carrier gasses used in the DART® experiment. A DART® MS experiment has a vacuum available. Unexpectedly, it was found that a jet separator could function to separate not only analyte molecules in a carrier gas stream but also positively and negatively charged analyte ions in a stream of carrier gas.

Figure 4A:
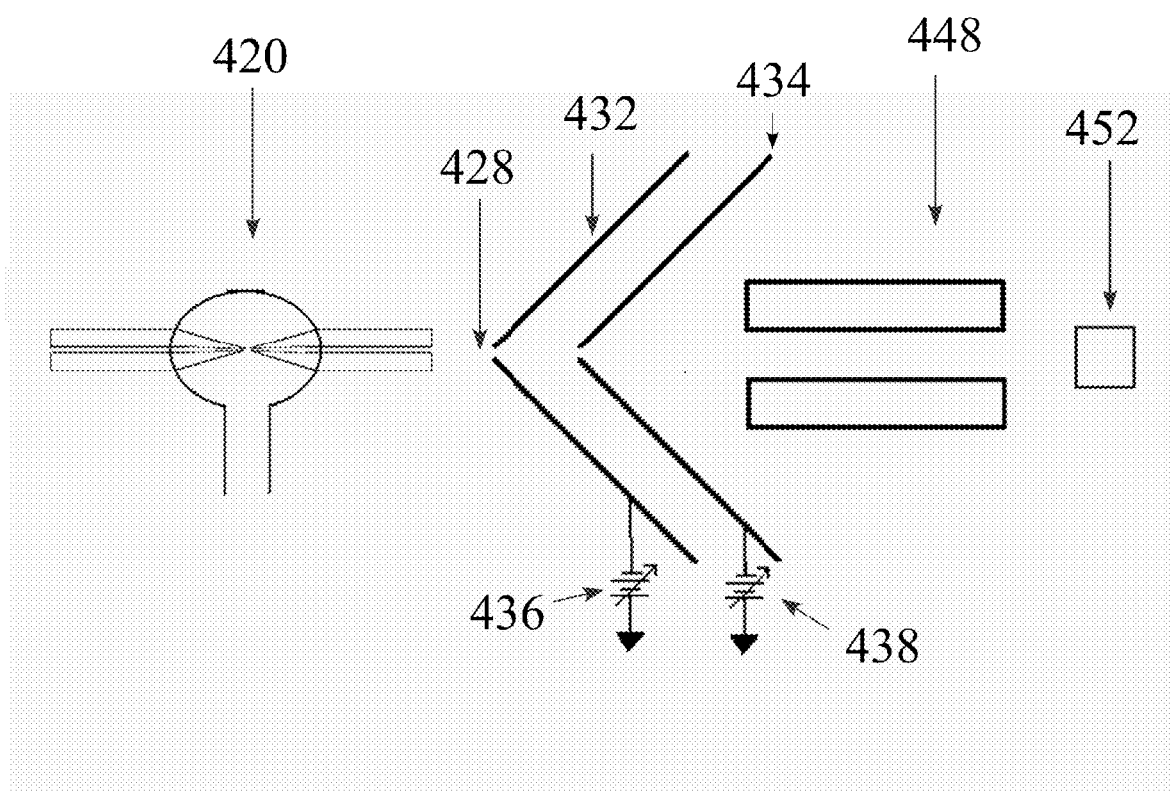
FIG. 4(A) is a schematic diagram of a jet separator as a means of transferring ions into a MS with skimmers-based API inlet in accordance with one embodiment of the present invention.

In embodiments of the invention, ions formed through desorption ionization in a stream of carrier gas are directed towards a target containing analyte molecules. In embodiments of the invention, the target can consist of one or more of the following classes of objects, a solid, a liquid, and a gas. FIG. 4(A) shows embodiments of the invention, where the analyte ions generated from the target are passed through a jet separator 420, enter an orifice 428, and a series of one or more skimmers 432, 434 with applied focusing potentials 436, 438 into a mass analyzer 448, and impact with an ion detector 452.

Figure 4B:
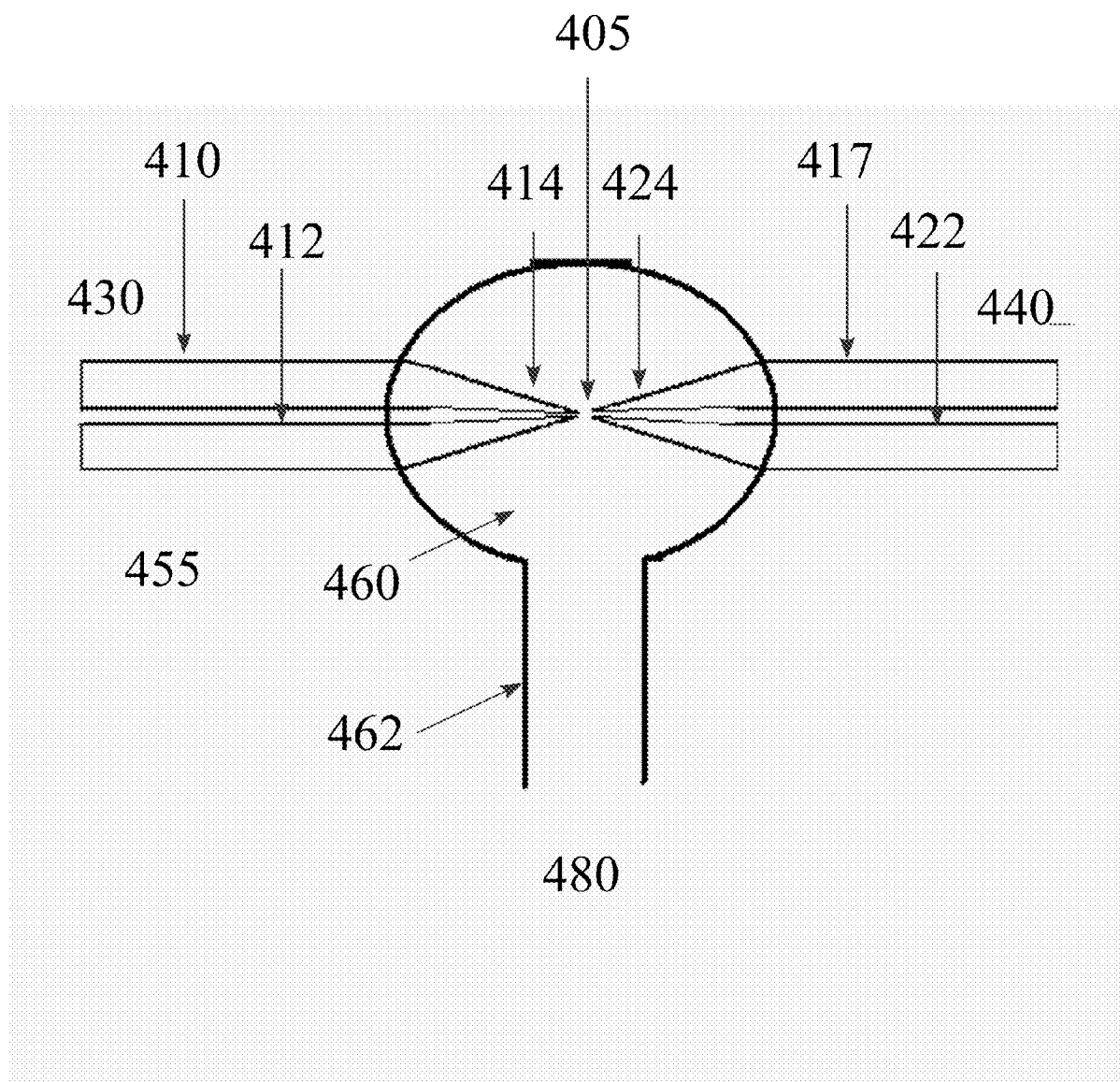
FIG. 4(B) is a schematic diagram of a jet separator as a means of transferring ions into a MS with a capillary-type API inlet in accordance with one embodiment of the present invention.

In embodiments of the invention, shown in FIG. 4(B) the analyte ions are formed in proximity to the inlet side of a jet separator 430. In embodiments of the invention, the ions will be sucked into a jet separator by a vacuum 480. In embodiments of the invention, an instrument can operate with the jet separator inlet side 430 at atmospheric pressure. In other embodiments of the invention, the inlet side 430 can operate at elevated pressure. In alternative embodiments of the invention, the inlet side 430 can operate at reduced pressure.

In one embodiment of the invention, a DART® source produces a large volume of Helium, air molecules and analyte ions of interest in the same volume. The difference between the mass of the carrier gases and the mass of the analyte of interest can be one to several orders of magnitude. Thus the lighter mass carrier gases can be adequately separated from the higher mass analyte ions by a jet separator based on the differences in the relative momentum. In another embodiment of the invention, the jet separator can preferentially enrich the stream of high mass ions in the atmosphere while removing the low mass solvent molecules and solvent related ions which have been formed in order to effect ionization of samples from a surface. In a further embodiment of the invention, the jet separator can preferentially enrich the stream of high mass ions in the atmosphere while removing the low mass solvent molecules and solvent related ions which have been formed in order to effect ionization of samples originating from an original source used to generate reagent ions. In one embodiment of the invention, one or more of the following carrier gases selected from the group consisting of methanol, dimethylsulfoxide and $H_2O$ solvent molecules are used with DART® and are separated out with a jet separator.

In embodiments of the invention, the incorporation of a jet separator enables the collection of larger volumes of gas containing ions for transfer of those ions to a high vacuum chamber of a mass spectrometer. As shown in FIG. 4(B), in embodiments of the invention the large volume of gas enters a gap 405 between an inlet 430 and an exit 440 side of a jet (gas) separator with the heavier mass ions and non-ionized molecules transiting the gap from inlet to exit side with greater efficiency than the lighter gas molecules and atoms. In embodiments of the invention, the jet (gas) separator is made up of two or more substantially co-axial tubes 410 and 417 with inner diameters 412 and 422. In embodiments of the invention, the tubes may have a reduced outside diameter at their respective ends 414 and 424. The jet (gas) separator is located in a region 462, which is under reduced pressure 460 compared with the outside region 455, due to the action of a vacuum 480. In one embodiment of the invention, a jet separator is used as an inlet for a conventional non-API-MS instrument. In another embodiment of the invention, a jet separator is used as an inlet for an API-MS instrument.

In embodiments of the invention, a mass spectrometer source can be operated with no ionization means. In an alternative embodiment of the invention, a mass spectrometer can have an ionization means including but not limited to electron impact, chemical ionization, and desorptive chemical ionization in either positive or negative ionization mode.

Figure 4C:
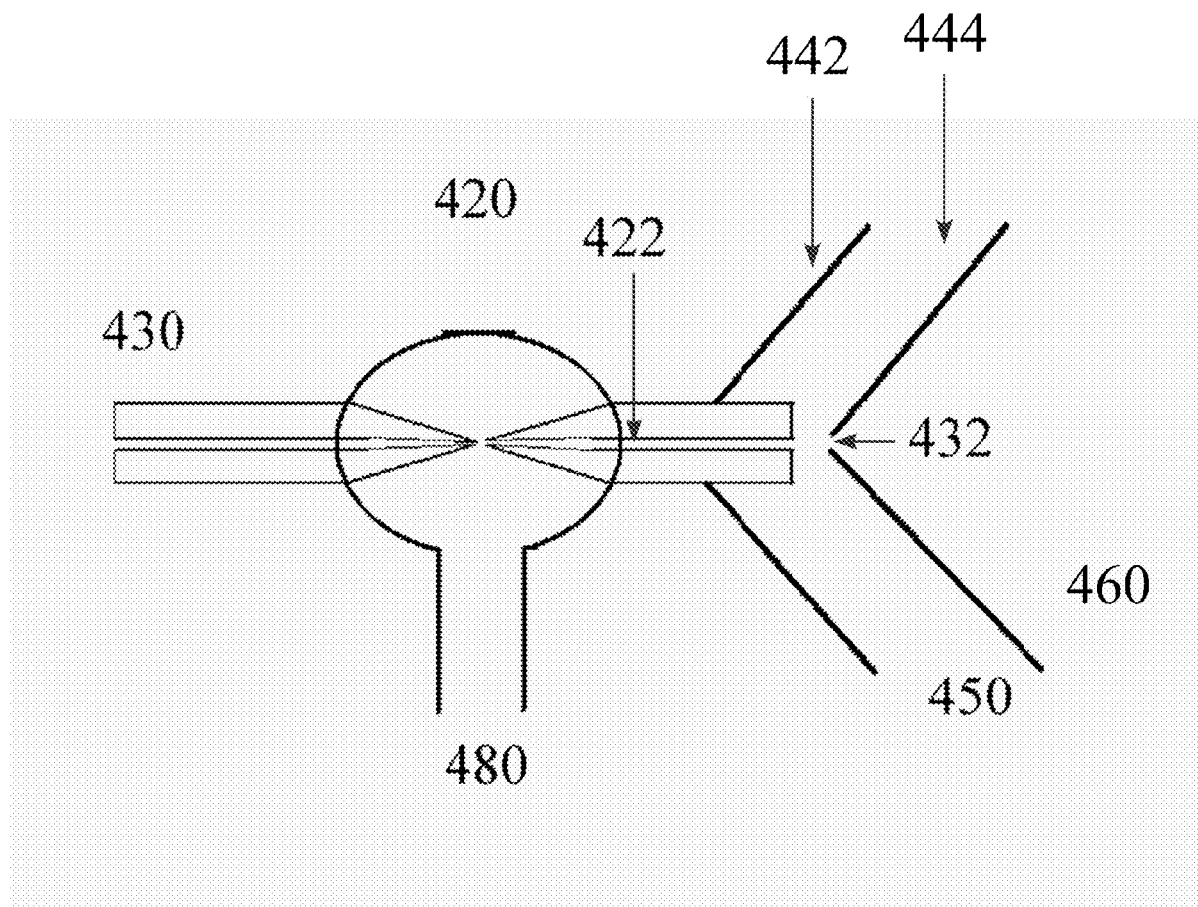
FIG. 4(C) is a schematic diagram of a jet separator as integrated with a conventional API-MS in accordance with one embodiment of the present invention.

FIG. 4(C) shows an embodiment of the invention, where the ionization source in FIG. 3 has been modified so that a vacuum stage 450 of an instrument includes a replacement of its skimmer 442 type orifice with an exit side inner tube orifice 422 of a jet (gas) separator 420 to form an inlet to that first moderate vacuum region 450 which is separated by another orifice 432 and skimmer 444 from a high vacuum region of a mass spectrometer 460 containing a mass analyzer. In embodiments of the invention, the inlet side 430 of a jet separator can be at atmospheric pressure and a vacuum is applied at 480.

Figure 17:
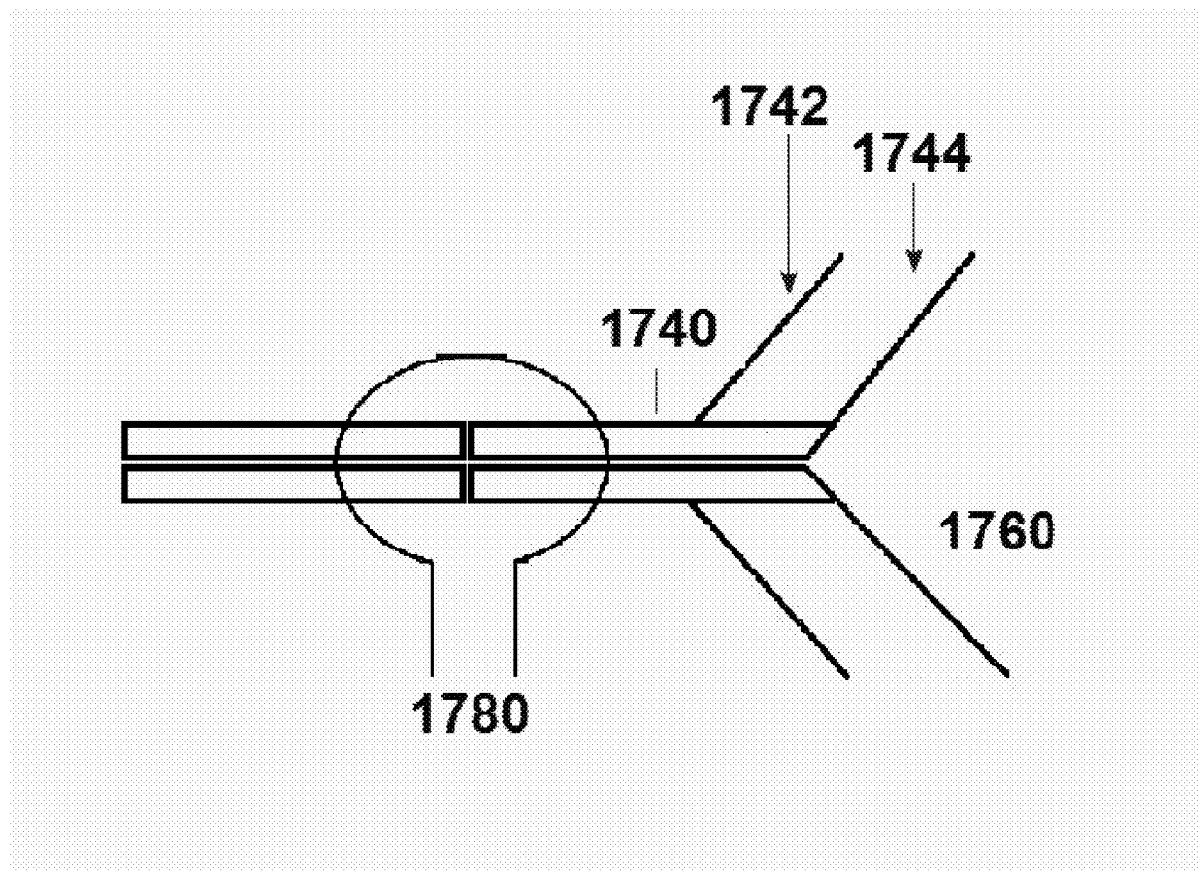
FIG. 17 is a schematic diagram of a jet separator where the outlet tube of the gas separator spans more than one skimmer in accordance with one embodiment of the present invention.

FIG. 17 shows an embodiment of the invention, where the API region of the instrument shown in FIG. 3 has been modified so that the exit tube 1740 of the gas separator is directly coupled to the high vacuum region of the mass spectrometer 1760 bypassing the two skimmers 1742, 1744 such that the gas and molecules entering the gas separator are subject to vacuum from both the gas separator vacuum pump 1780 and the mass spectrometer system 1760.

A gas separator can include a jet separator combined with an external ion source. A gas separator has the advantage that it can increase the number of ions transmitted from an external ion source into a mass spectrometer without deleteriously affecting the performance of the mass spectrometer. By increasing the diameter of a tube(s) used to transmit the ions from the external ion source into the mass spectrometer more ions can be transmitted. By incorporating a gas separator into the tube to transportions to the mass spectrometer, the high vacuum region of the mass spectrometer can be minimally disturbed (or otherwise remain undisturbed). The gas separator can act to pump away neutral atoms and small molecules present in the stream of ions being transported from the external ion source to the mass spectrometer.

EXAMPLE 1

Application of a Potential to a Jet Separator

Figure 5:
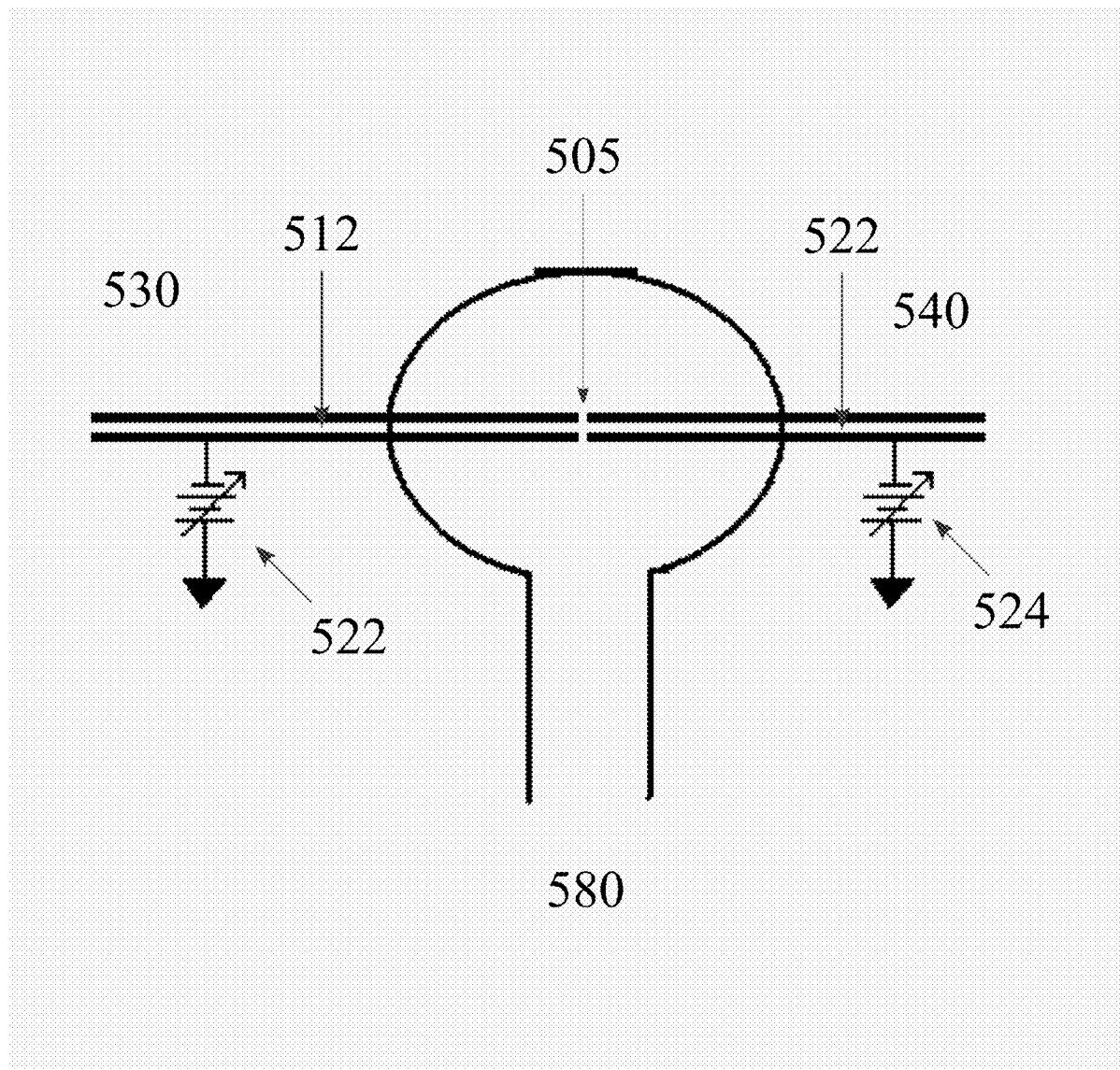
FIG. 5 is a schematic diagram showing a jet separator fabricated with inlet and exit tubes in accordance with one embodiment of the present invention.

FIG. 5 shows an embodiment of the invention where an inlet side and an exit side of a jet separator can be operated at ground potential, at positive potential or negative potential. In an embodiment of the invention, one or more tubes which make up the jet separator can be electrically charged, a jet separator can be designed with an inlet 530 and exit 540 to permit uniform application of potentials 522 and 524 and thereby a uniform field in the gap 505 under a vacuum 580. In an embodiment of the invention, a potential applied to metal surfaces of an inlet and an exit tube can be the same potential in order to provide for maximum ion transfer. In an alternative embodiment of the invention, a potential applied to metal surface of an inlet 522 and an exit line 524 can differ from each other in order to provide for maximum ion transfer. In an alternative embodiment of the invention, the gap 505 may be increased in length in order to provide for maximum ion transfer. In an alternative embodiment of the invention, the diameter of the inlet 530 and exit 540 may have different internal diameters 512, 522 from each other in order to provide for maximum ion transfer.

Figure 14:
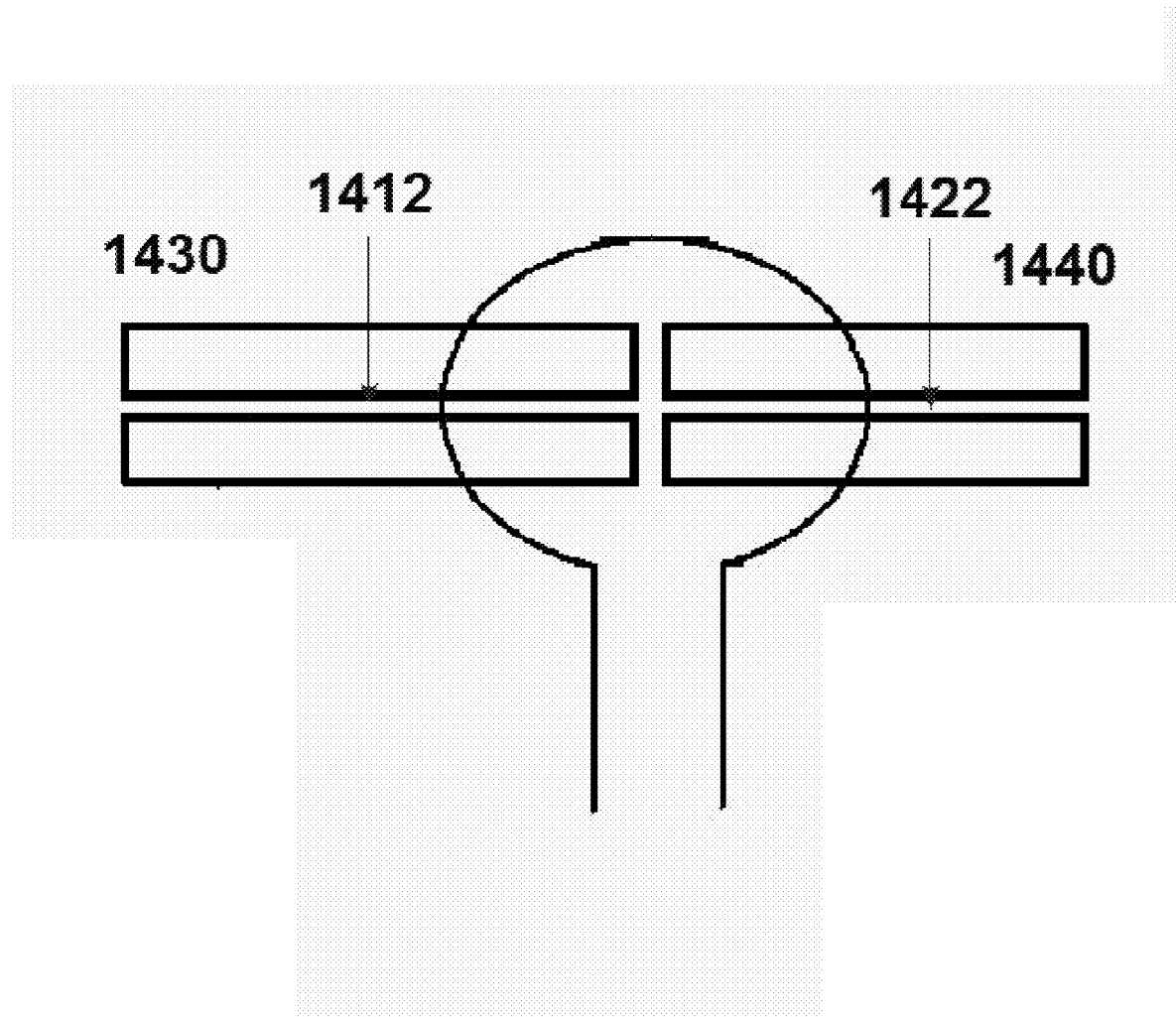
FIG. 14 is a schematic diagram showing a jet separator fabricated with inlet and outlet tubes having thicker diameter tubes compared with FIG. 4(c) in accordance with one embodiment of the present invention.
Figure 15:
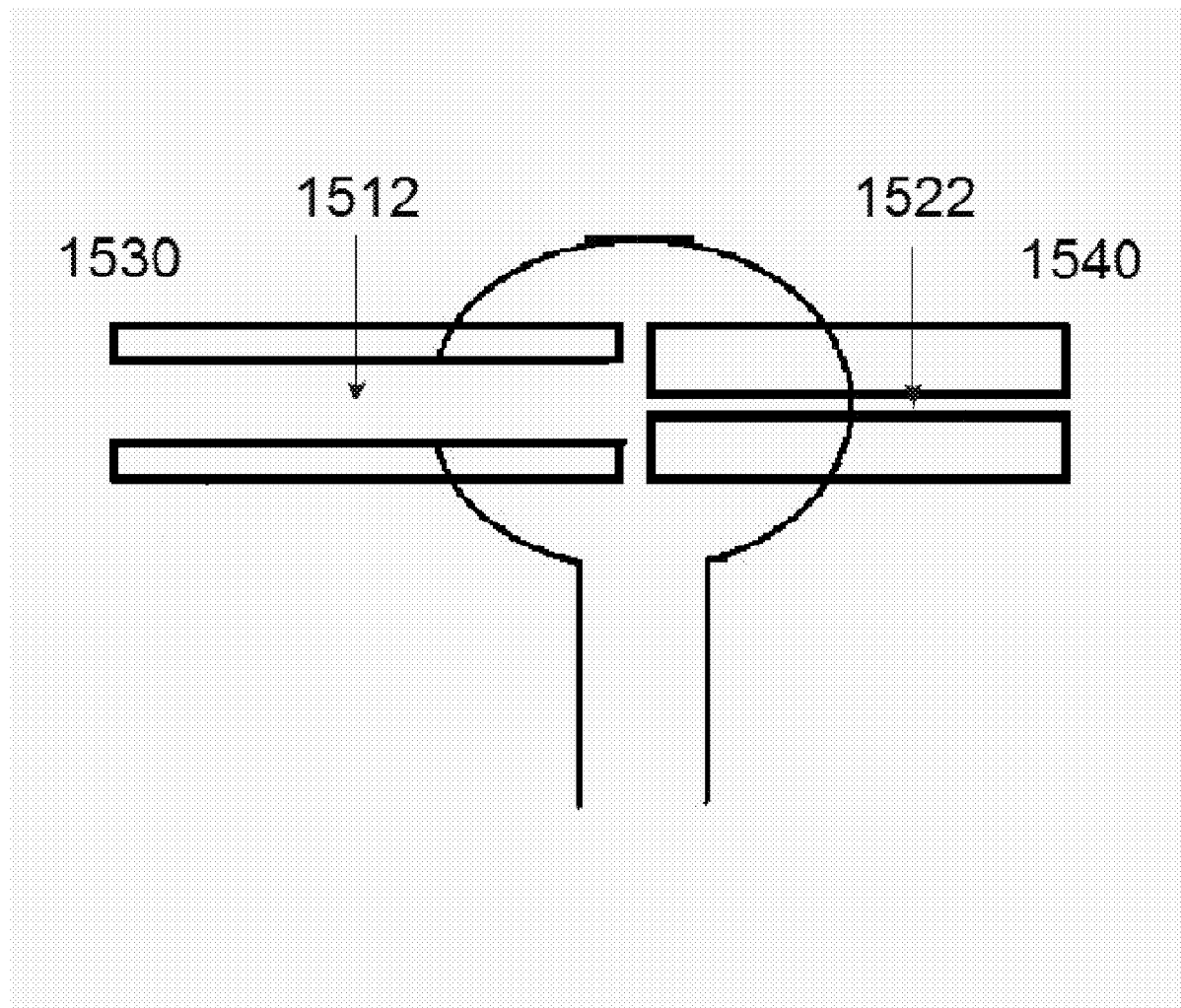
FIG. 15 is a schematic diagram showing a jet separator fabricated with inlet and outlet tubes having different inner diameter tubes in accordance with one embodiment of the present invention.
Figure 16:
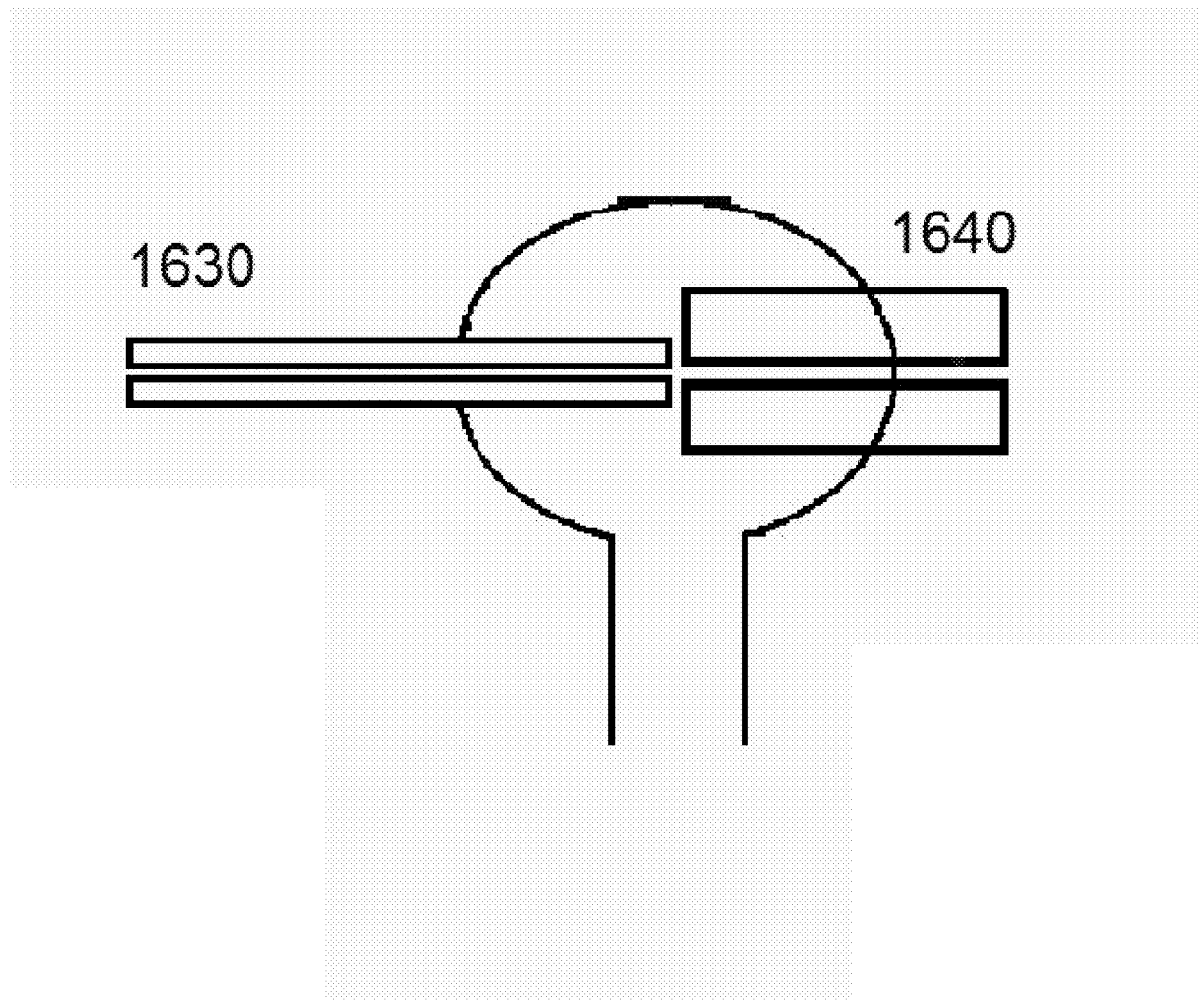
FIG. 16 is a schematic diagram showing a jet separator fabricated with inlet and outlet tubes having different lengths in accordance with one embodiment of the present invention.

FIG. 14 shows an embodiment of the invention where the outer diameter of the inlet tube 1430 and an outlet tube 1440 have a large diameter relative to the inner diameter 1412, 1422 of the respective tubes. In another embodiment of the invention FIG. 15 the inner diameter 1512 of the inlet 1530 and inner diameter 1522 of the outlet 1540 tubes can be different. In another embodiment of the invention, FIG. 16, the length of the inlet 1630 and outlet 1640 tubes can be different to provide for more efficient collection of gasses and molecules for analysis.

In Example 1, the jet separator can be replaced with a gas separator.

EXAMPLE 2

Handling High Carrier Gas Volume

Figure 6:
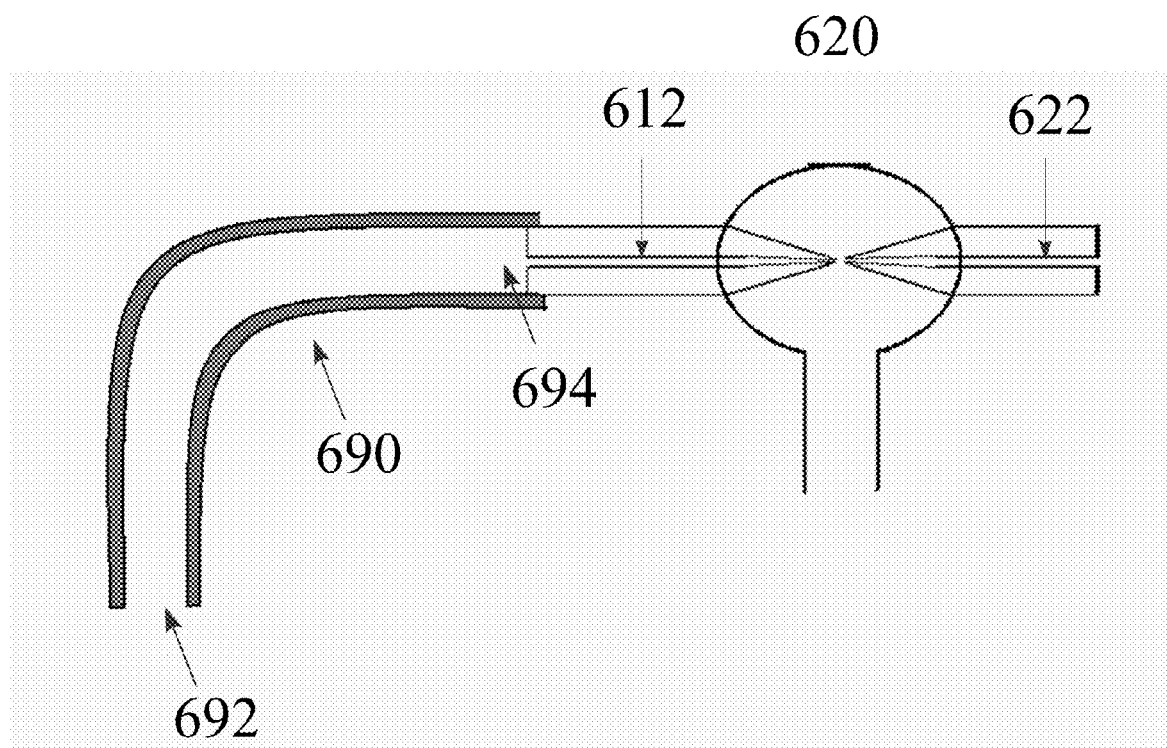
FIG. 6 is a schematic diagram showing an embodiment of the present invention where a jet separator is connected with a sampling tube.

FIG. 6 shows an embodiment of the invention with a jet separator inlet extension sampling tube 690. In an embodiment of the invention, a jet separator inlet extension sampling tube 690 increases the ability to draw carrier gas containing metastable neutral excited-state species, air molecules, sample related molecules and sample related ions from longer distances into the mass spectrometer. In an embodiment of the invention, the jet separator inlet extension sampling tubing 690 is linear. In an embodiment of the invention, the jet separator inlet extension sampling tubing 690 is curved. In an embodiment of the invention, the jet separator inlet extension sampling tubing 690 is flexible. In an embodiment of the invention, the jet separator inlet extension sampling tubing 690 is heated. In an embodiment of the invention, the jet separator inlet extension sampling tubing 690 is operated at ambient temperature. In an embodiment of the invention, the jet separator inlet extension sampling tubing 690 can be metal, flexible metal, ceramic, plastic, flexible plastic or combinations thereof. In an embodiment of the invention, the jet separator inlet extension sampling tubing can range in length from 10 millimeters to 10 meters or more. In an embodiment of the invention, the jet separator inlet extension sampling tubing 690 can be made of non-woven materials. In an embodiment of the invention, the jet separator inlet extension sampling tubing 690 can be made from one or more woven materials. In prior art, capillary transfer lines with limited diameter and short length have been used to achieve transfer of ion generated during surface ionization directly into the mass spectrometer by a combination of electrical potential and vacuum action. In an embodiment of the invention, a jet separator with a narrow inlet side inside diameter 612 is used to restrict gas flow entering the mass spectrometer 622 allowing the jet separator 620, to give optimum enrichment of ions for transfer to a mass spectrometer. In an embodiment of the invention, a jet separator with wider inside diameter 612 is used on an inlet side to increase gas flow into a jet separator 620 irrespective of whether it functions ideally as a jet separator, in that less than optimum enrichment of ions for transfer to a mass spectrometer can be acceptable in order to improve flow of gas containing ions through a jet separator inlet extension sampling tube 690. In an embodiment of the invention, the jet separator inlet extension sampling tube inlet inside diameter 692 and exit inside diameter 694 can be different in order to increase efficiency of transfer of ions across a distance in the presence of carrier and atmospheric gases.

In Example 2, the jet separator can be replaced with a gas separator.

EXAMPLE 3

Metal Grid Enhancement of a Jet Separator

Figure 7:
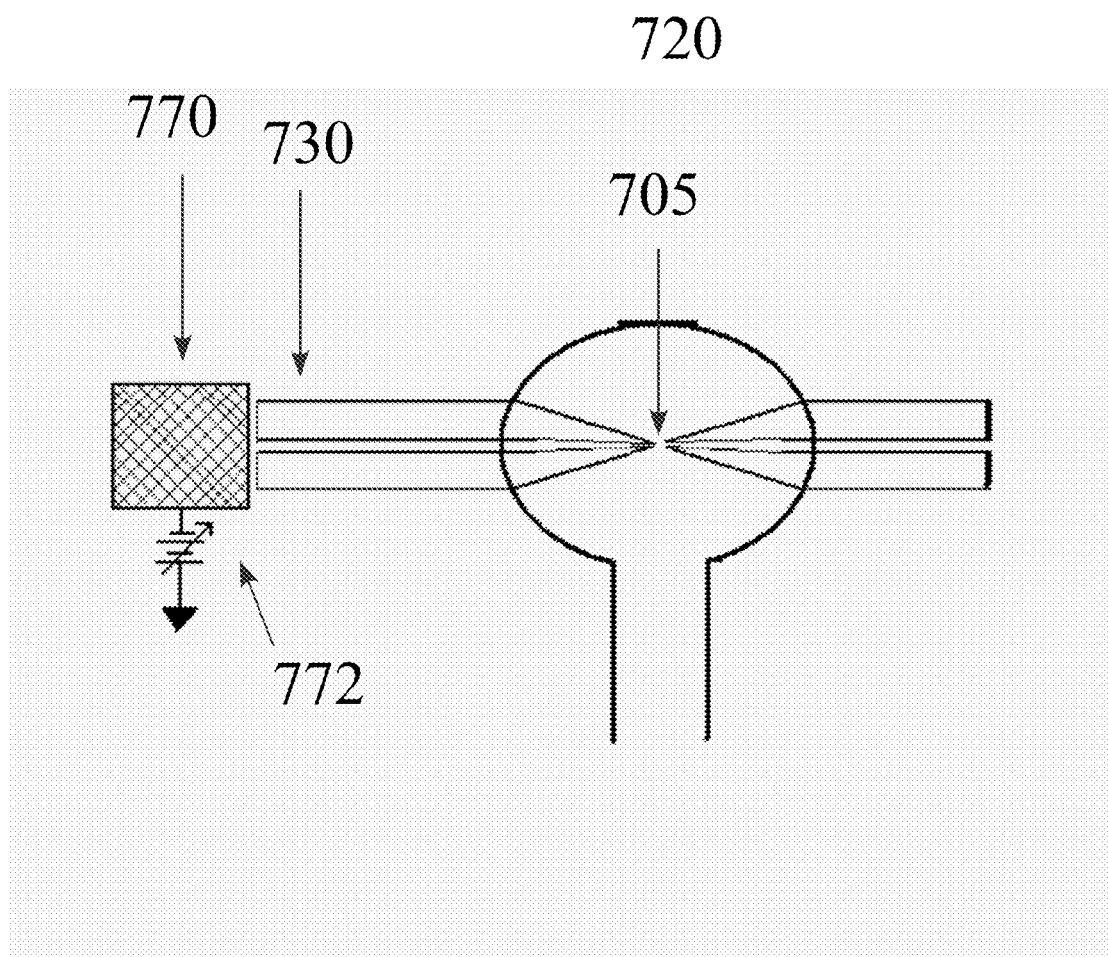
FIG. 7 is a schematic diagram showing a jet separator with the grid at its inlet in accordance with one embodiment of the present invention.

FIG. 7 shows embodiments of the invention, where collection of ions for sampling by a mass spectrometer, via a jet separator, is improved by addition of a grid surrounding an ionization area in a desorption ionization experiment. In an embodiment of the invention, the grid is made of an open ended mesh cage 770. In an embodiment of the invention, the mesh cage is cylindrical in shape. In an embodiment of the invention, the grid is made of metal. In an embodiment of the invention, the mesh cage is wire. In an embodiment of the invention, the metal wire mesh cage can be operated at ground potential. In an embodiment of the invention, the metal wire mesh cage can be operated at positive potential 772 as required for constraining the ions of interest generated from a sample. In an embodiment of the invention, the metal wire mesh cage can be operated at a negative potential 772 as required for constraining the ions of interest generated from a sample. In an embodiment of the invention, the metal wire mesh cage is in contact with one or both of an inlet and an outlet tube of a jet separator. In an embodiment of the invention, the metal wire mesh cage is not in contact with either an inlet or an outlet tube of a jet separator. In an embodiment of the invention, a cage of metal mesh 770 encircles and extends from an end of a jet separator inlet 730 for use in improving efficiency of collection of ions generated at an inlet of a jet separator 720. In an embodiment of the invention, a cage can be supported by overlapping either inlet or exit tubes to bridge a gap 705 completely, or be mounted as a physical extension of a tube.

Figure 8:
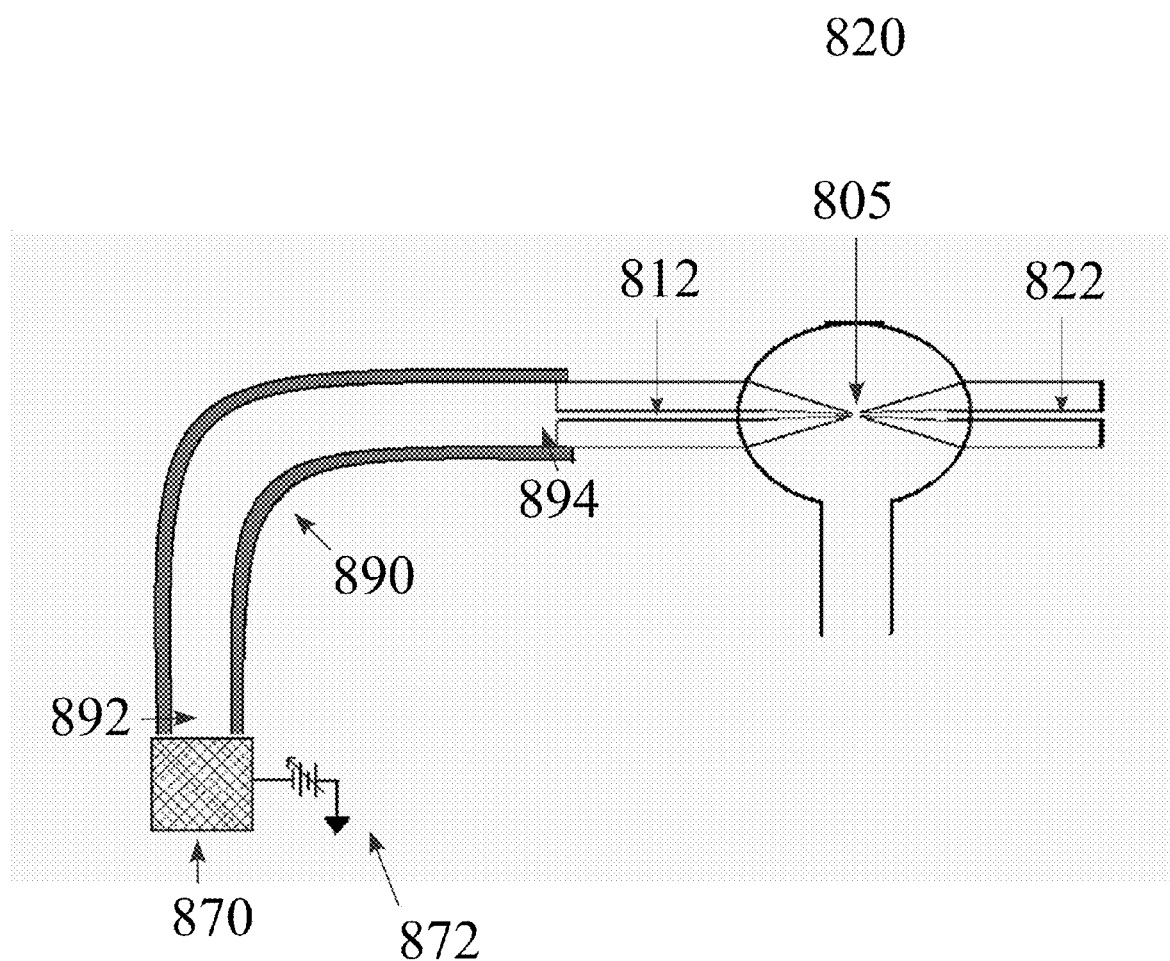
FIG. 8 is a schematic diagram showing a jet separator with a grid at the inlet of the sampling tub in accordance with one embodiment of the present invention.

FIG. 8 shows embodiments of the invention where a grid surrounding an ionization area in the desorption ionization experiment is remote from the jet separator 820. In an embodiment of the invention, the grid is made of an open ended mesh cage 870. In an embodiment of the invention, the mesh cage is cylindrical in shape. In an embodiment of the invention, the grid is made of metal. In an embodiment of the invention, the mesh cage is wire. In an embodiment of the invention, the metal wire mesh cage can be operated at ground potential. In an embodiment of the invention, the metal wire mesh cage can be operated at positive potential 872 as required for constraining the ions of interest generated from a sample. In an embodiment of the invention, the metal wire mesh cage can be operated at a negative potential 872 as required for constraining the ions of interest generated from a sample. In an embodiment of the invention, the metal wire mesh cage is in contact with one or both of an inlet and an outlet tube of a jet separator. In an embodiment of the invention, the metal wire mesh cage is not in contact with either an inlet or an outlet tube of a jet separator. In an embodiment of the invention, the cage encircles and extends from an end of a jet separator inlet extension sampling tube 890 for use in improving efficiency of collection of ions generated at positions remote from an inlet of a jet separator 820. In an embodiment of the invention, a cage can be mounted at a location in between the end of a jet separator inlet extension sampling tube 892 and the inlet 894 of a jet separator 820. In an embodiment of the invention, a wire mesh cage acts to enhance transfer of ions between an inlet tube 812 and an exit tube 822. In an embodiment of the invention, a cage can be supported by overlapping either inlet or exit tube to bridge a gap 805 completely, or be mounted as a physical extension of a tube.

In Example 3, the jet separator can be replaced with a gas separator.

EXAMPLE 4

Application of Fields to Metal Grid

Figure 9:
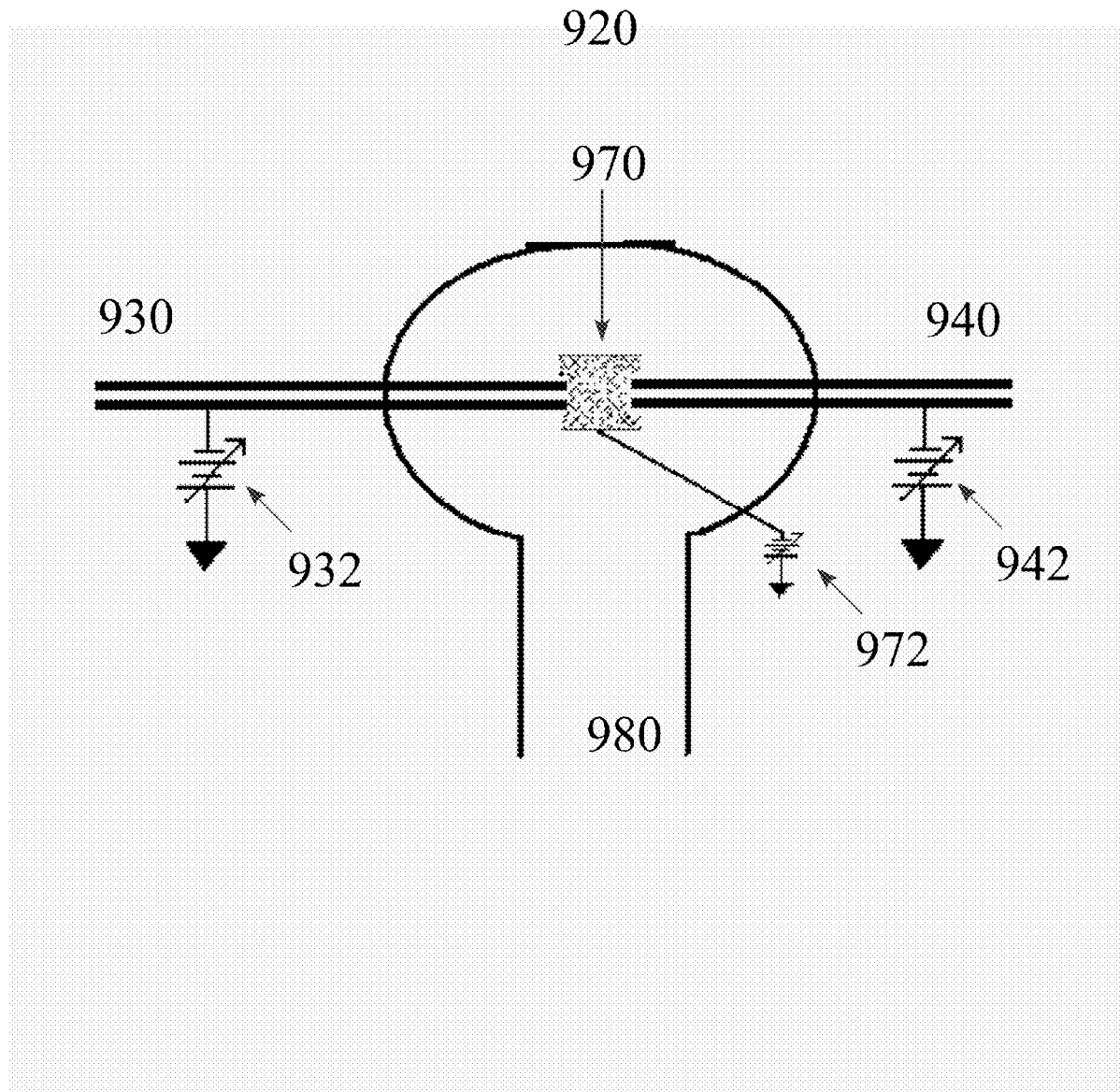
FIG. 9 is a schematic diagram of a jet separator fabricated with a grid between the inlet and exit tubes in accordance with one embodiment of the present invention.

FIG. 9 shows embodiments of the invention where the gap between an inlet side 930 and an exit side 940 of a jet separator 920 is spanned by a grid 970. In an embodiment of the invention, a potential 932 and 942 is applied to the inlet side 930 and an exit side 940 respectively of a jet separator 920. In an embodiment of the invention, the grid is made of an open ended mesh cage 970 allowing passage of gas atoms and neutral molecules to a low pressure vacuum region 980 of a jet separator 920. In an embodiment of the invention, the mesh cage is cylindrical in shape. In an embodiment of the invention, the grid is made of metal. In an embodiment of the invention, the mesh cage is wire. In an embodiment of the invention, the metal wire mesh cage can be operated at ground potential 972. In an embodiment of the invention, the metal wire mesh cage can be operated at positive potential 972 as required for constraining the ions of interest generated from a sample. In an embodiment of the invention, the metal wire mesh cage can be operated at a negative potential 972 as required for constraining the ions of interest generated from a sample. In an embodiment of the invention, the metal wire mesh cage is in electrical and or physical contact with one or both of an inlet and an outlet tube of a jet separator. In an embodiment of the invention, the metal wire mesh cage is not in electrical and/or physical contact with either an inlet or an outlet tube of a jet separator. In an embodiment of the invention, the electric field inside the metal wire mesh cage is homogeneous. In an embodiment of the invention, the electric field inside the metal wire mesh cage is non-homogeneous. In an embodiment of the invention, a magnetic field is generated inside the cage. Ions generated inside of a cage are constrained in a volume of the cage for a longer period of time thus increasing a potential for their collection in a volume of gas being sucked into an inlet of a jet separator. In alternative embodiments of the invention, a wire mesh cage does not span the gap between an inlet side 930 and an exit side 940 of a jet separator 920.

In Example 4, the jet separator can be replaced with a gas separator.

EXAMPLE 5

Application of an Ion Guide

In other embodiments of the invention, an ion guide spans the gap between an inlet side and an exit side of a jet separator. In an embodiment of the invention a direct current voltage is applied to the ion guide. In other embodiments of the invention a radio frequency voltage is applied to the ion guide.

In Example 5, the jet separator can be replaced with a gas separator. In an embodiment of the invention the gas separator further comprises an ion guide. The advantage of the ion guide is that ions are transmitted efficiently along the length of the guide while atoms and neutral molecules remain unaffected and thus a vacuum will have a greater tendency to strip away neutral molecules from entering the outlet side of the gas separator. Thus the ion guide increases the transmission of ions from the inlet tube to the outlet tube of the gas separator.

EXAMPLE 6

Vaporization of Molecules through Heating

In embodiments of the invention, the collection of molecules for transfer to an area of ionization is completed by subjecting an area at a terminus of an inlet suction tube to a high temperature source including a heat lamp, flame, various types of lasers, heat source activated by use of an electrical circuit and other heat sources capable of applying heat to a surface. In an embodiment of the invention, sample molecules collected by the action of a vacuum provided by a jet separator are subsequently ionized by the action of the desorption ionization source as a carrier gas containing metastable neutral excited-state species, air molecules, sample related molecules and sample related ions mix along a transfer tube.

In Example 6, the jet separator can be replaced with a gas separator.

EXAMPLE 7

Vaporization of Molecules in a Closed System

In embodiments of the experiment, volatile molecules are dispersed in an atmosphere around a sample in a uniform, unfocused manner. A stream of gas is used to force a gas containing vaporized molecules through an exit into a sampling tube where a carrier gas containing metastable neutral excited-state species generated by the desorption ionization source is present and being drawn towards a inlet of a jet separator. Interaction of the volatilized molecules with a desorption ionization carrier gas results in ionization of those molecules in a sampling tube and subsequent transfer of those ions into an inlet of a jet separator for enrichment as they are transferred into a mass spectrometer.

In Example 7, the jet separator can be replaced with a gas separator.

EXAMPLE 8

Vaporization of Molecules in a Closed System

Figure 10:
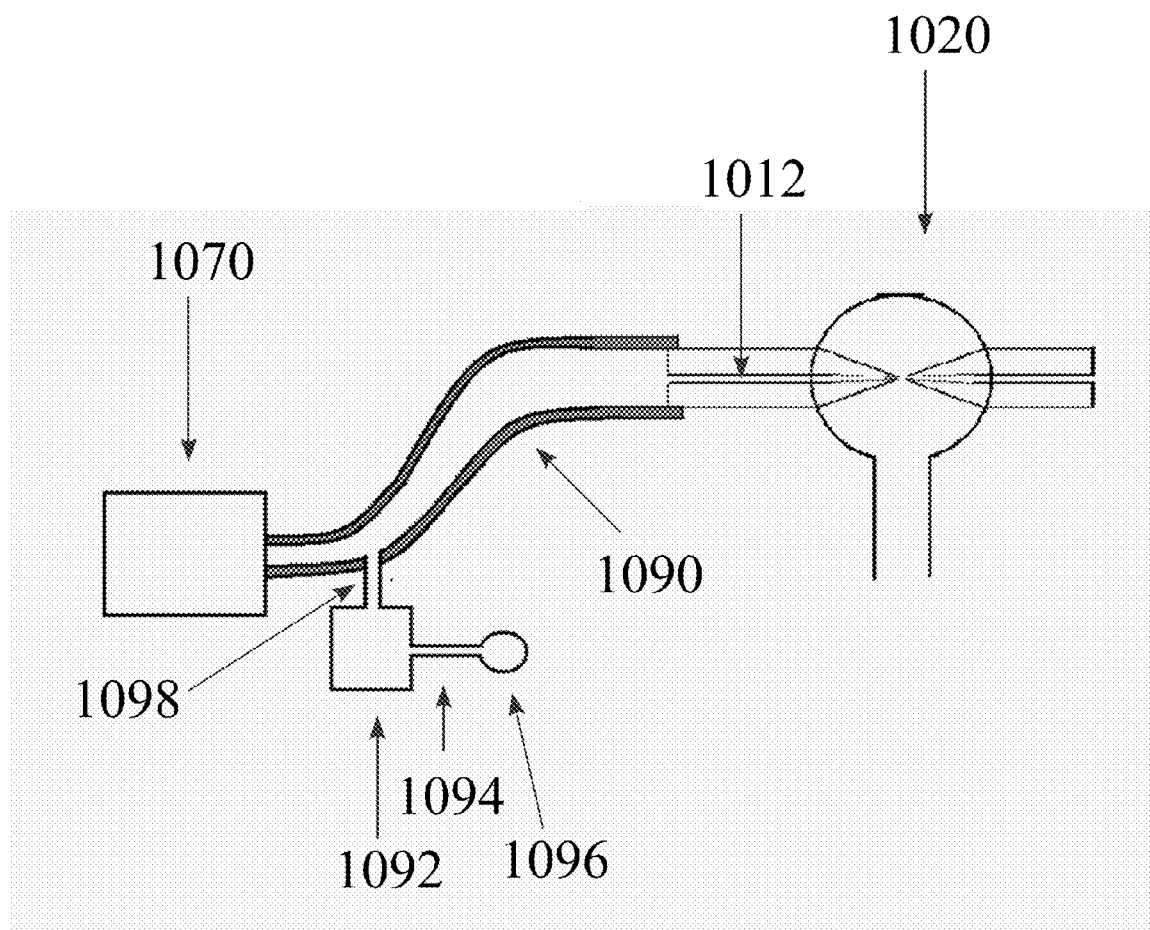
FIG. 10 is a schematic diagram of a jet separator with a sampling tube and a grid and the sample connected to the sampling tube at a point intermediate the grid and the jet separator in accordance with one embodiment of the present invention.
Figure 11:
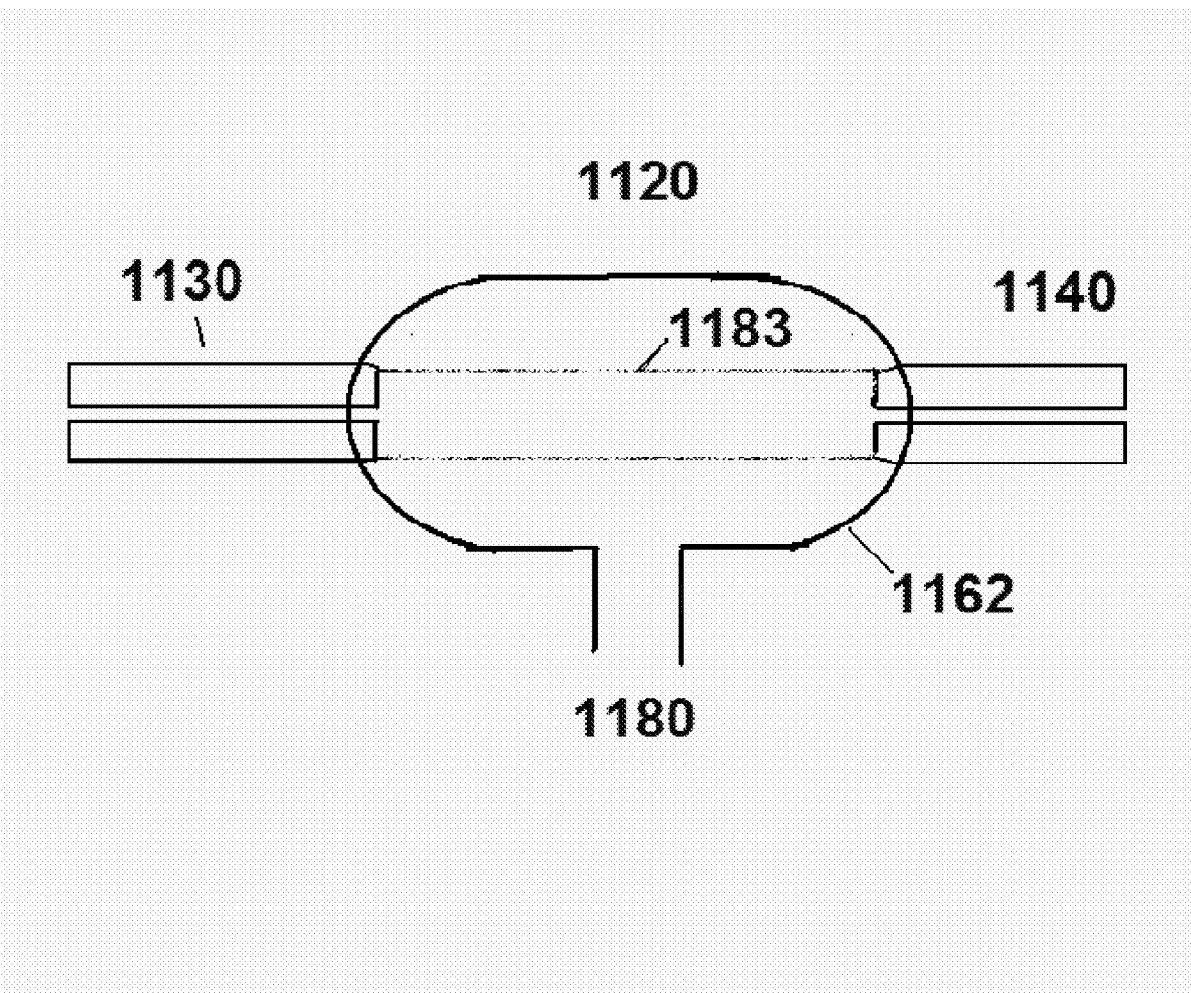
FIG. 11 is a schematic diagram showing an effusion type separator in accordance with one embodiment of the present invention.

FIG. 10 shows embodiments of the invention, where a sample is enclosed in a chamber 1092 where volatile molecules from that sample are free to disperse into the volume of the chamber atmosphere. The sample chamber may either completely surround the sample or be constructed in such a manner that it makes an enclosure when placed on an object such as a flat surface. The sample may be at ambient temperature, subject to high temperature source including a heat lamp, flame, various types of lasers, heat source activated by use of an electrical circuit and other heat sources capable of applying heat to a sample or frozen in the case of extremely volatile samples. The vaporized molecules either leave the chamber 1092 exiting through tube 1098 by their own action or may be forced by the flow of a gas originating from a device 1096, entering the chamber through tube 1094, to exit through tube 1098 into the volume of the transfer tube 1090 at a point along its length that is between the source 1070 and the jet separator 1020. The tube 1090 is attached to a source 1070, which is generating a carrier gas containing metastable neutral excited-state species that is flowing into the attached transfer tube 1090 at its terminus. Interaction of volatile sample molecules and carrier gas containing metastable neutral excited-state species in the sampling tube 1090 results in ionization of the sample molecules along the volume of the sampling tube. The ions formed in the volume of 1090 enter into the inlet 1012 of a jet separator for enrichment as they are transferred into a mass spectrometer In an alternate configuration FIG. 11 we envision the use of an effusion type gas separator 1120. In this device an inlet tube 1130 of variable internal diameter is attached to a porous glass tube 1183 to which an exit tube 1140 is attached so as to permit flow of gas containing ions through the length of the gas separator. The porous glass tube is surrounded by an evacuation chamber 1162 which is connected to a vacuum pump 1180. Gasses and ions enter gas separator through the inlet 1130 traveling towards the mass spectrometer. As the gas containing sample passes through the porous region the smaller gas molecules and atoms are removed by diffusion through into the low vacuum region 1162.

Figure 12:
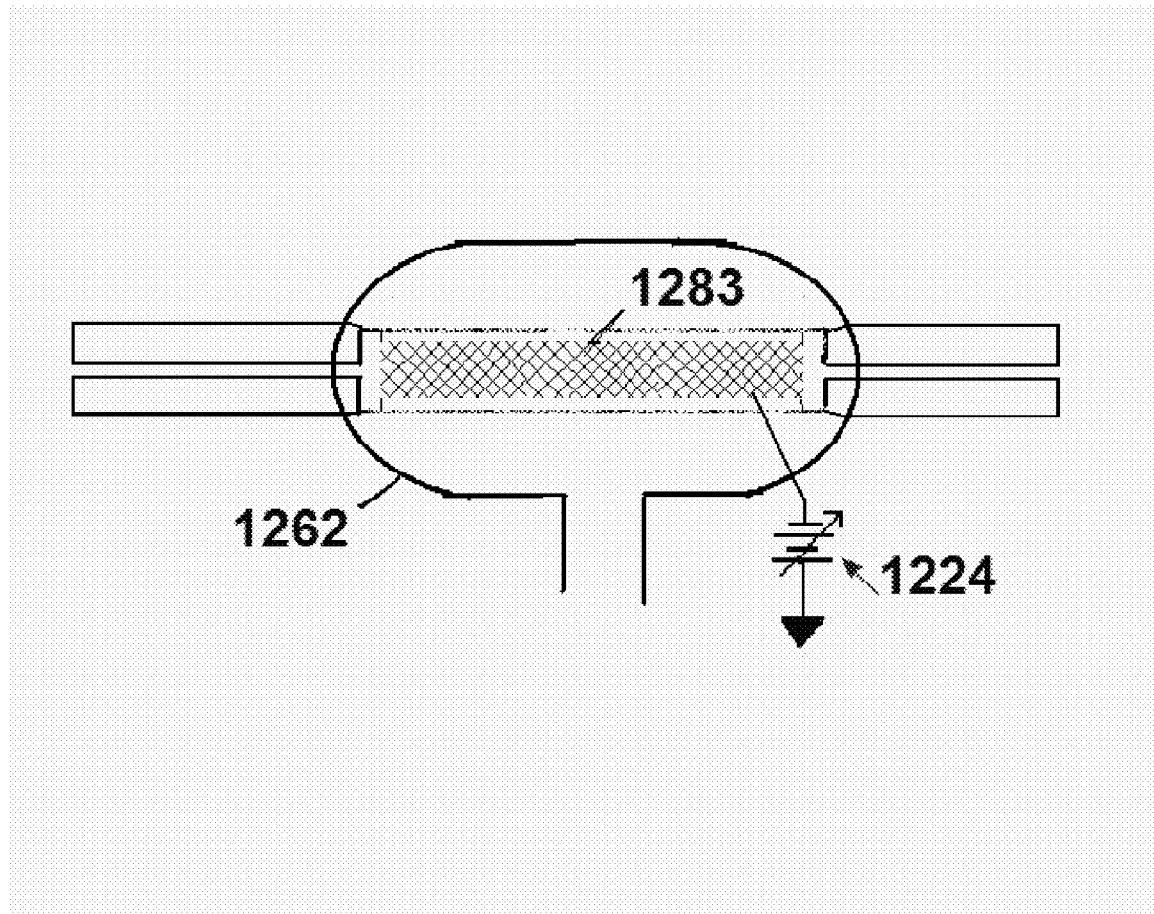
FIG. 12 is a schematic diagram showing an effusion type separator incorporating a wire mesh cage to which a potential can be applied in accordance with one embodiment of the present invention.

In an alternative configuration FIG. 12 a metal screen cylinder 1283 to which a potential 1224 can be applied is positioned inside the volume of the porous tube to enable retention of ions by keeping an equal potential around the ions as they travel through the gas separator inside the volume of the tube while permitting the neutral carrier gas to diffuse into the pumping region 1262.

Figure 13:
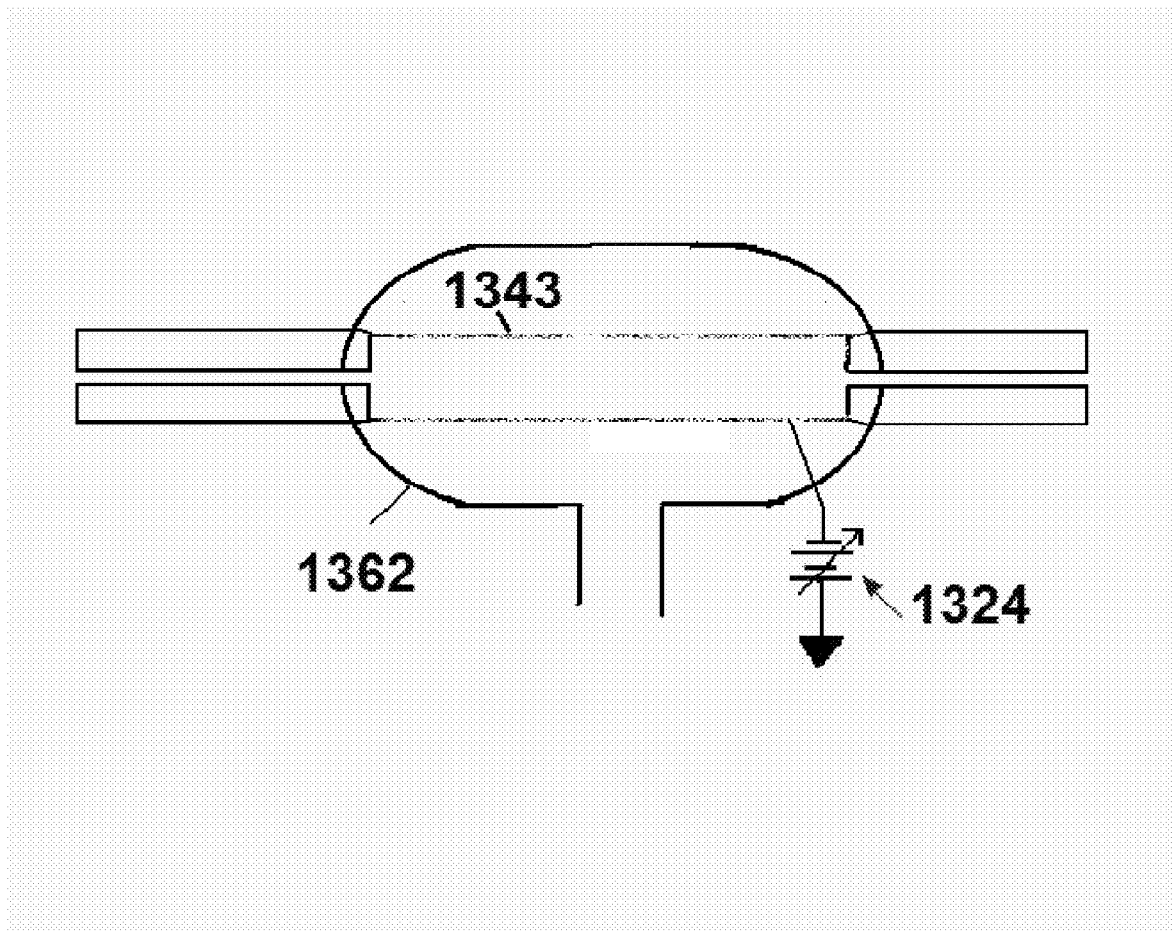
FIG. 13 is a schematic diagram showing an effusion type separator incorporating a perforated cage to which a potential can be applied in accordance with one embodiment of the present invention.

In alternative embodiments of the invention FIG. 13 porous glass tubes, plastic sieves, glass, machinable glass and ceramics, and porous ceramic to which a metal film or coating can be applied, metal mesh, glass lined metal tubes, metal coated fused silica, metal coated machinable glass, and metal coated ceramic 1343 to which a potential 1324 can be applied on its inside diameter surface is used to retain the ions while pumping away the neutrals as they diffuse through the porous tube into the pumping region 1362.

In Example 8, the jet separator can be replaced with a gas separator.

EXAMPLE 9

Transfer of Ions Through the Gas Separator

Figure 18:
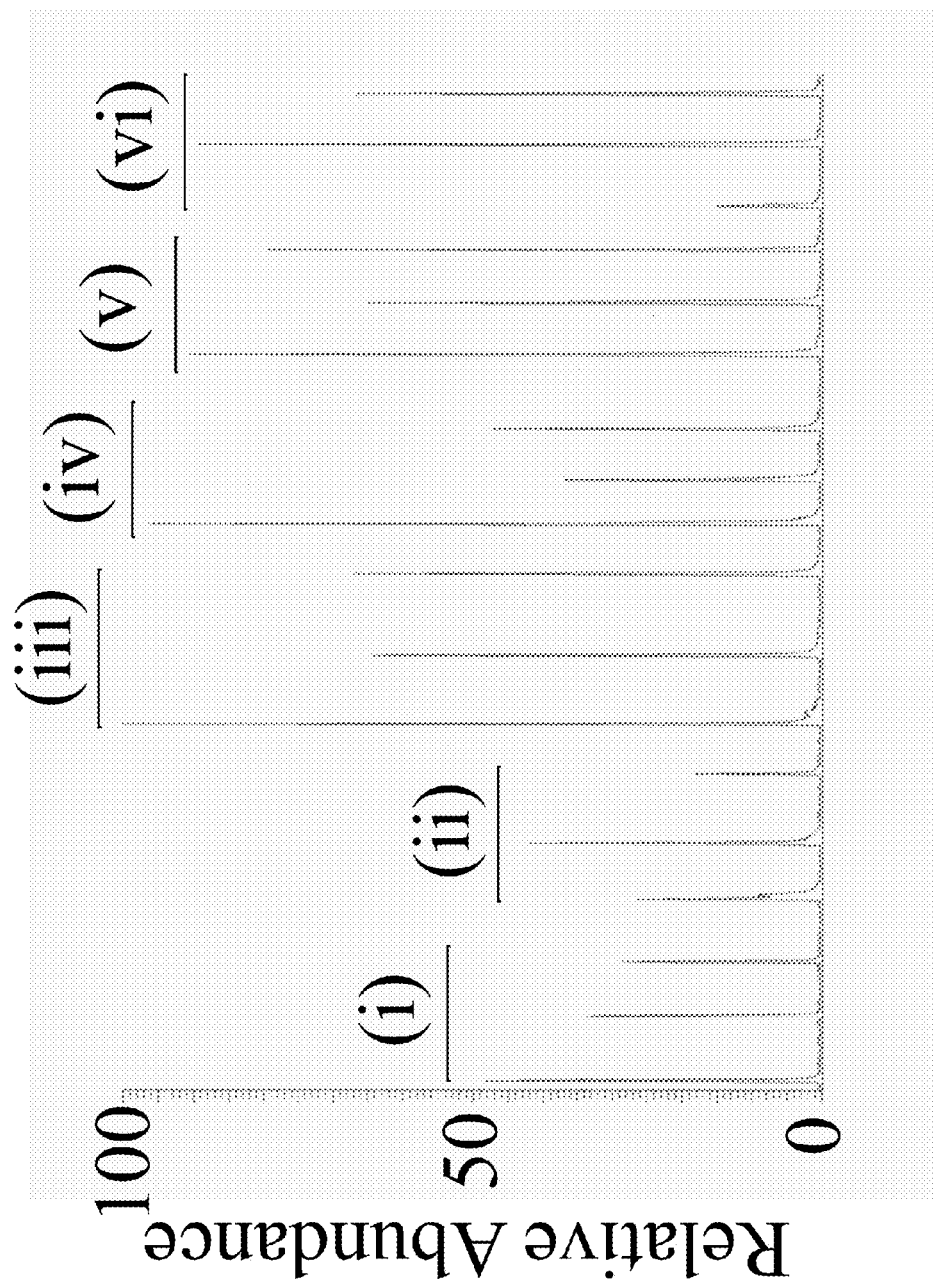
FIG. 18 (i)-(vi) is the mass chromatogram trace of the relative abundance of ions sampled from the ionization region as a function of the potential applied to the surface of the inlet and outlet tube of the gas separator.

Results of the application of an equal potential to both the inlet and outlet tube of the gas separator are shown in FIG. 18 where the mass chromatogram of the protonated quinine molecule ion is plotted as a function of the potential applied to the inner and outer surface of the gas separator tubes. A ing sample of quinine inserted in a glass melting point tube was introduced in front of the DART® source and ionized at atmospheric pressure. The potential applied to the inlet and outlet tubes was raised and the relative abundance of the molecule was measured over time. The voltage applied to the tube for each sample is indicated above each series of peaks, where (i) indicates 0 volts applied, (i) indicates 50 V, (ii) indicates 100 V, (iii) indicates 200 V, (iv) indicates 300 V, (v) indicates 400 V and (vi) indicates 500 V. This indicates the unexpected result that a (relatively high) potential applied to a gas separator can increase the number of ions transmitted from atmospheric ionization sources into a mass spectrometer analyzer region. The experiment further indicates that at lower potential ranging from 0 to 50V the relative abundance of the protonated molecule is reduced with respect to the abundance of ions detected at higher potentials ranging from 100 to 400V.

Figure 19:
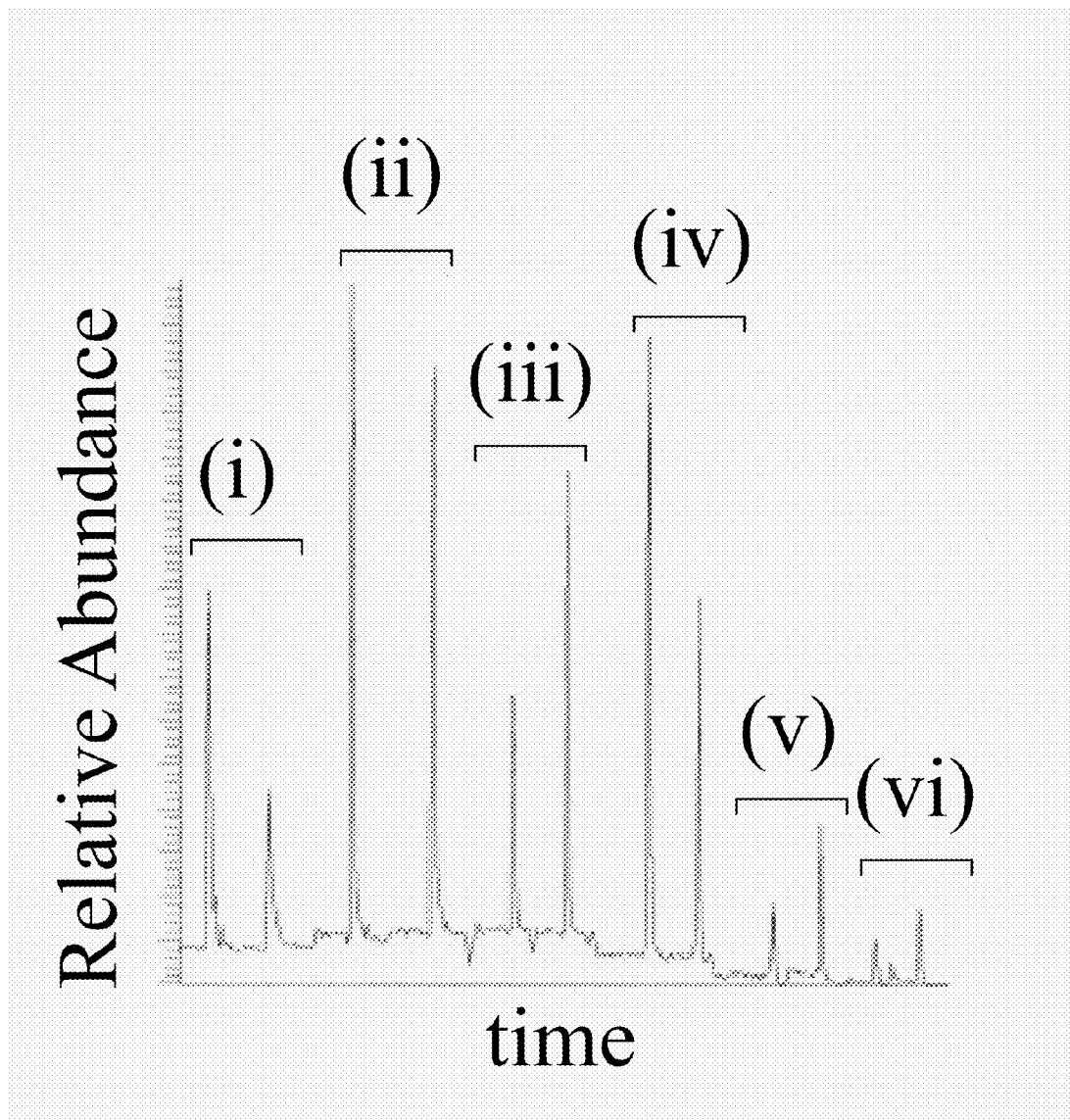
FIG. 19 (i)-(vi) is a total ion chromatogram trace of the relative abundance of ions sampled from the ionization region as a function of the relative vacuum being applied between the inlet and outlet tubes of the gas separator.

The placement of two tubes on-axis with one another between the atmospheric pressure ionization region and the high vacuum inlet of the mass spectrometer results in a population of those ions being transferred into the mass spectrometer for analysis. In the experiment we understand that there are two different vacuum sources in the gas separator. As the gas carrying neutral atoms, and molecules, charged atoms and molecules and metastable atoms and molecules exits the inlet tube they can either be pulled into the outlet tube where they are transferred to the mass spectrometer or pulled into the low pressure region of the separator where they exit into the vacuum pump. The differential pressure of each region is combined to evacuate the inlet tube. The experimental results plotted in FIG. 19 show the effect of increasing the vacuum applied in the region between the inlet tube and the outlet tube on ion transmission into the mass spectrometer. A valve is used to adjust the vacuum applied to the gas separator. In FIG. 19, the TIC trace in the region (i) corresponds with 0 turn of the valve, region (ii) corresponds with 1 turn of the valve, region (iii) corresponds with 2 turns of the valve, region (iv) corresponds with 3 turns of the valve, region (v) corresponds with 4 turns of the valve and region (vi) corresponds with 5 turns of the valve. This experiment indicates the unexpected result that a vacuum applied to the gas separator can increase the number of ions transmitted from atmospheric ionization sources into mass spectrometer analysis regions. The results also show that as the valve is opened and the vacuum increases, the transmission of ions into the mass spectrometer increases (see regions (ii), (iii) and (iv)). However, further opening of the valve results in reduced transmission as shown in regions (v) and (vi). The data also shows that as the vacuum is further increased it has the effect where more of the sample ions are being diverted away from the mass spectrometer. This value is observed to vary as a function of the distance between the inlet and outlet tubes of the gas separator. For a specific geometry the vacuum can be adjusted in order to provide optimum transfer of ions through the outlet tube of the gas separator into the mass spectrometer.

Figure 20:
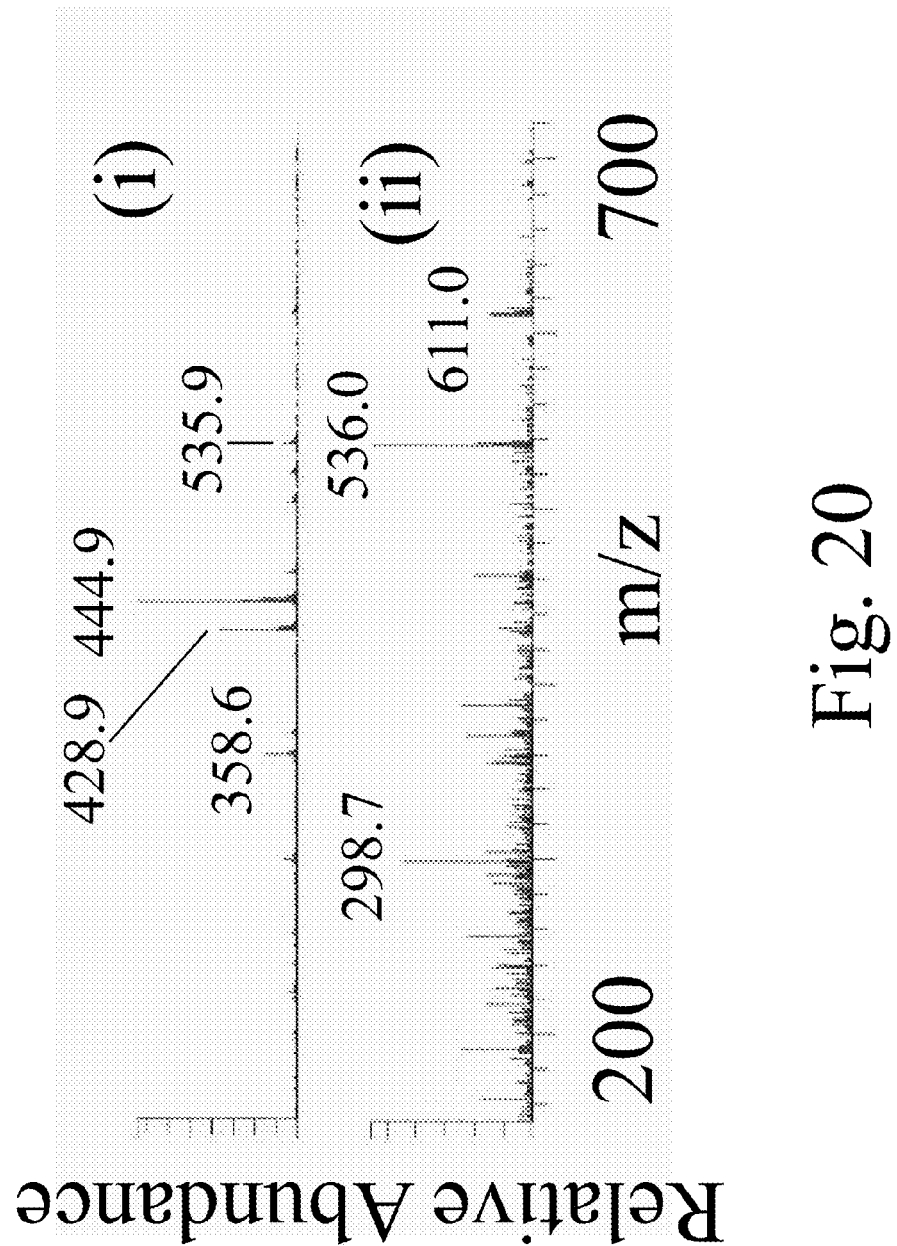
FIG. 20 shows the mass spectra derived from the ionization of ambient atmosphere (i) after and (ii) prior to application of a vacuum to the gas separator.

The DART® source enables ionization of materials remote to the API inlet of the mass spectrometer, however in instances where the distance is increased the abundance of ions derived from the ambient atmosphere is pronounced with respect to those derived from the sample of interest. Enabling the use of long inlet tubes for sampling remote regions by extending the DART® source operating zone away form the immediate API-inlet area of the mass spectrometer is shown to reduce the contribution of molecules present in the ambient atmosphere is shown in FIG. 20 where the a comparison of the mass spectrum generated (i) with and (ii) without the gas separator functioning is shown. In FIG. 20 (ii) ions derived from normal laboratory air dominate the mass spectrum while those ions are present at reduced levels once a vacuum (FIG. 20 (i)) is applied to the region between the inlet and outlet tubes in the vacuum on condition. This experiment indicates an unexpected result that increasing the volume of gas sampled at the opening of the inlet tube can increase the number of ions transmitted from atmospheric ionization sources into mass spectrometer analysis regions and thereby the overall sensitivity of analysis.

Advantages

An advantage of the gas separator can be the ability to increase the volume of gas sampled and introduced into the high vacuum region of the MS. Because atoms and small neutral molecules can be stripped away from ions in the gas separator, the high vacuum can remain unaffected while the sensitivity of analysis increases.

Uses

The gas separator can be combined with a variety of atmospheric ionization sources including DART®, DESI and atmospheric pressure MALDI used in MS. In each case by increasing the number of ions introduced into the MS, the sensitivity of the technique can be increased. The gas separator can also be used in a number of other spectroscopic devices that rely on transferring ions formed at approximately atmospheric pressure or low vacuum to regions of high vacuum for detection. The gas separator can also be used in surface science spectroscopic devices that preferably operate at ultra high vacuum where ions formed by a process that introduces a gas would be deleterious and therefore removal of the gas would be beneficial. The gas separator can also be used with other suitable detectors including a raman spectrometer, an electromagnetic absorption spectrometer, an electromagnetic emission spectrometer and a surface detection spectrometer. The kinds of analyte detectors that can be used with a gas separator are not limited to those specified but include those detectors that a person having ordinary skill in the art would envisage without undue experimentation.

Wire mesh cage includes a perforated tube where the holes can be machined or alternatively a porous ceramic, etc. The term "based on" as used herein, means "based at least in part on", unless otherwise specified.

A capacitive surface is a surface capable of being charged with a potential. A surface is capable of being charged with a potential, if a potential applied to the surface remains for the typical duration time of an experiment, where the potential at the surface is greater than 50% of the potential applied to the surface.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. For example, it is envisaged that, irrespective of the actual shape depicted in the various Figures and embodiments described above, the outer diameter exit of the inlet tube can be tapered or non-tapered and the outer diameter entrance of the outlet tube can be tapered or non-tapered.

Thus, the breadth and scope of the present invention should not be limited by any of the above-described exemplary embodiments, but should be defined only in accordance with the following claims and their equivalents.

What is claimed is:

1. A gas ion separator comprising:
   (a) at least two substantially co-axial tubes, where a proximal tube of the at least two substantially co-axial tubes is positioned closest to an external ionization source and a distal tube of the at least two substantially co-axial tubes is positioned furthest from the external ionization source, where the proximal tube and the distal tube are spaced such that there is a gap between the proximal tube and the distal tube, where a vacuum region is operably connected to the gap; and
   (b) an ion guide operably connected to the proximal tube.

2. The gas ion separator of claim 1, where the ion guide is operably connected to the proximal tube and the distal tube.

3. The gas ion separator of claim 2, where the ion guide is operably connected to the distal tube.

4. The gas ion separator of claim 1, where the gap is spanned by the ion guide.

5. The gas ion separator of claim 1, further comprising a potential is applied to the ion guide.

6. The gas ion separator of claim 1, where the proximal tube is positioned between a region of approximately atmospheric pressure and a region of approximately high vacuum.

7. The gas ion separator of claim 1, further comprising a direct current voltage is applied to the ion guide.

8. The gas ion separator of claim 1, further comprising a radio frequency voltage is applied to the ion guide.

9. The gas ion separator of claim 1, further comprising a capacitive surface on one or both the proximal tube and the distal tube.

10. The gas ion separator of claim 9, further comprising a potential applied to the capacitive surface.

11. A gas ion separator comprising three or more substantially co-axial tubes and an ion guide, where the three or more substantially co-axial tubes are spaced such that there is one or more gaps between at least two of the three or more substantially co-axial tubes, where a proximal tube of the three or more substantially co-axial tubes is positioned closest to an external ionization source, where at least one of the one or more gaps is operably connected to a vacuum region and where the ion guide is operably connected to the proximal tube.

12. The gas ion separator of claim 11, where the proximal tube is positioned between a region of approximately atmospheric pressure and a region of approximately high vacuum.

13. The gas ion separator of claim 12, where the ion guide spans at least one of the one or more gaps.

14. The gas ion separator of claim 11, where the ion guide is operably connected to the distal tube.

15. The gas ion separator of claim 11, further comprising a capacitive surface on one or more of the three or more substantially co-axial tubes.

16. The gas ion separator of claim 15, further comprising a potential applied to the ion guide.

17. A spectroscopic device comprising:
   (a) an external ionization source;
   (b) a spectroscopic analyzer;
   (c) a proximal tube closest to the external ionization source and a distal tube furthest from the external ionization source, where the proximal tube and the distal tube are substantially co-axial, where the proximal tube and the distal tube are spaced such that there is a gap between the proximal tube and the distal tube;
   (d) an ion guide operably connected to one or both the proximal tube and the distal tube; and
   (e) a vacuum region operably connected to the gap.

18. The spectroscopic device of claim 17, where the ion guide is made of metal.

19. The spectroscopic device of claim 17, where the gap is spanned by the ion guide.

20. The spectroscopic device of claim 17, where a potential is applied to the ion guide.

* * * * *